US012036402B2

(12) United States Patent
Hoffman et al.

(10) Patent No.: US 12,036,402 B2
(45) Date of Patent: Jul. 16, 2024

(54) COCHLEAR IMPLANTS INCLUDING ELECTRODE ARRAYS AND METHODS OF MAKING THE SAME

(71) Applicant: ADVANCED BIONICS AG, Staefa (CH)

(72) Inventors: Paul Vincent Hoffman, Valencia, CA (US); Matthew Vadim Krywcun, Saugus, CA (US); Uli Gommel, Valencia, CA (US); James George Elcoate Smith, Santa Clarita, CA (US)

(73) Assignee: Advanced Bionics AG, Staefa (CH)

( * ) Notice: Subject to any disclaimer, the term of this patent is extended or adjusted under 35 U.S.C. 154(b) by 449 days.

(21) Appl. No.: 17/407,350

(22) Filed: Aug. 20, 2021

(65) Prior Publication Data

US 2021/0379365 A1    Dec. 9, 2021

Related U.S. Application Data

(63) Continuation of application No. 16/463,957, filed as application No. PCT/US2017/064231 on Dec. 1, 2017, now Pat. No. 11,123,551.

(60) Provisional application No. 62/428,668, filed on Dec. 1, 2016.

(51) Int. Cl.
*A61N 1/05* (2006.01)
*A61N 1/36* (2006.01)
*A61N 1/375* (2006.01)

(52) U.S. Cl.
CPC ....... *A61N 1/0541* (2013.01); *A61N 1/36038* (2017.08); *A61N 1/3752* (2013.01)

(58) Field of Classification Search
None
See application file for complete search history.

(56) References Cited

U.S. PATENT DOCUMENTS

| | | | |
|---|---|---|---|
| 5,123,422 | A | 6/1992 | Charvin |
| 5,702,373 | A | 12/1997 | Samson |
| 6,119,044 | A | 9/2000 | Kuzma |
| 6,144,883 | A | 11/2000 | Kuzma |
| 6,421,569 | B1 | 7/2002 | Treaba et al. |
| 6,451,014 | B1 | 9/2002 | Wakikaido et al. |

(Continued)

FOREIGN PATENT DOCUMENTS

| | | |
|---|---|---|
| CN | 101889910 A | 11/2010 |
| CN | 102958562 A | 3/2013 |

(Continued)

OTHER PUBLICATIONS

PCT International Search and Written Opinion dated Jun. 18, 2018 for PCT App. Ser. No. PCT/US2017/064231.

(Continued)

*Primary Examiner* — Ankit D Tejani
(74) *Attorney, Agent, or Firm* — Henricks Slavin LLP

(57) ABSTRACT

A method of forming a cochlear implant electrode array includes positioning a contact array assembly, which includes at least one carrier and a plurality of contacts on the at least one carrier, in a mold, removing at least a portion of the at least one carrier from the mold without removing the plurality of contacts from the mold, and introducing resilient material into the mold after the at least a portion of the at least one carrier has been removed to form a flexible body.

10 Claims, 26 Drawing Sheets

(56) References Cited

U.S. PATENT DOCUMENTS

| | | |
|---|---|---|
| 7,881,811 B2 | 2/2011 | Risi |
| 8,249,724 B2 | 8/2012 | Risi et al. |
| 8,812,121 B2 | 8/2014 | Risi et al. |
| 8,868,213 B2 | 10/2014 | Shan et al. |
| 8,880,187 B2 | 11/2014 | McDonald et al. |
| 8,880,193 B1 * | 11/2014 | Thenuwara .......... A61N 1/0541 607/57 |
| 9,033,869 B2 | 5/2015 | Thenuwara et al. |
| 9,037,267 B2 | 5/2015 | Thenuwara et al. |
| 9,050,457 B2 | 6/2015 | Foster et al. |
| 9,211,403 B2 | 12/2015 | Tortonese et al. |
| 9,415,207 B2 | 8/2016 | Thenuwara et al. |
| 9,492,654 B2 | 11/2016 | Thenuwara et al. |
| 9,937,345 B2 | 4/2018 | Knisely et al. |
| 10,994,138 B2 | 5/2021 | Walter et al. |
| 11,103,704 B2 | 8/2021 | Walter et al. |
| 11,123,551 B2 | 9/2021 | Hoffman et al. |
| 2002/0029074 A1 | 3/2002 | Treaba et al. |
| 2003/0032997 A1 | 2/2003 | Pianca et al. |
| 2007/0135884 A1 | 6/2007 | Risi |
| 2008/0004684 A1 | 1/2008 | Dadd et al. |
| 2009/0030483 A1 | 1/2009 | Risi et al. |
| 2010/0204768 A1 | 8/2010 | Jolly et al. |
| 2010/0318167 A1 | 12/2010 | Conn et al. |
| 2011/0016710 A1 | 1/2011 | Dadd et al. |
| 2011/0071596 A1 * | 3/2011 | Kara .................. B82Y 5/00 607/57 |
| 2011/0137393 A1 | 6/2011 | Pawsey et al. |
| 2011/0144733 A1 | 6/2011 | Dadd et al. |
| 2011/0264183 A1 * | 10/2011 | Gibson ................ A61N 1/0541 607/137 |
| 2011/0295352 A1 | 12/2011 | Thenuwara et al. |
| 2012/0221088 A1 | 8/2012 | Thenuwara et al. |
| 2013/0090711 A1 | 4/2013 | Ramachandran et al. |
| 2013/0245740 A1 | 9/2013 | Ramachandran et al. |
| 2014/0005599 A1 | 1/2014 | Sage et al. |
| 2014/0094892 A1 | 4/2014 | Thenuwara et al. |
| 2014/0163662 A1 | 6/2014 | Beerling et al. |
| 2014/0277275 A1 | 9/2014 | Djunaedi et al. |
| 2016/0015965 A1 | 1/2016 | Leavens |
| 2016/0022990 A1 | 1/2016 | Risi |
| 2018/0200517 A1 | 7/2018 | Knisely et al. |
| 2019/0275325 A1 | 9/2019 | Walter et al. |
| 2019/0329028 A1 | 10/2019 | Walter et al. |
| 2020/0384262 A1 | 12/2020 | Hoffman et al. |
| 2021/0353944 A1 | 11/2021 | Walter et al. |

FOREIGN PATENT DOCUMENTS

| | | |
|---|---|---|
| CN | 104644330 A | 5/2015 |
| EP | 1189560 A1 | 3/2002 |
| EP | 2303397 B1 | 4/2014 |
| WO | WO 96/31087 A1 | 10/1996 |
| WO | WO 00/71063 A1 | 11/2000 |
| WO | WO 2007/027879 A1 | 3/2007 |
| WO | WO 2009/065127 A1 | 5/2009 |
| WO | WO 2009/079704 A1 | 7/2009 |
| WO | WO 2012/003295 A1 | 1/2012 |
| WO | WO 2015/030734 A1 | 3/2015 |
| WO | WO 2018/031025 A2 | 2/2018 |
| WO | WO 2018/089272 A1 | 5/2018 |
| WO | WO 2018/102695 A2 | 6/2018 |

OTHER PUBLICATIONS

U.S. Appl. No. 16/463,957, filed May 24, 2019, U.S. Pat. No. 11,123,551 B2.
U.S. Appl. No. 17/407,350, filed Aug. 20, 2021, 2021/0379365 A1.
U.S. Appl. No. 16/343,496, filed Apr. 19, 2019, U.S. Pat. No. 10,994,138 B2.
U.S. Appl. No. 16/406,721, filed May 8, 2019, U.S. Pat. No. 11,103,704 B2.
U.S. Appl. No. 17/383,867, filed Jul. 23, 2021, 2021/0353944 A1.

* cited by examiner

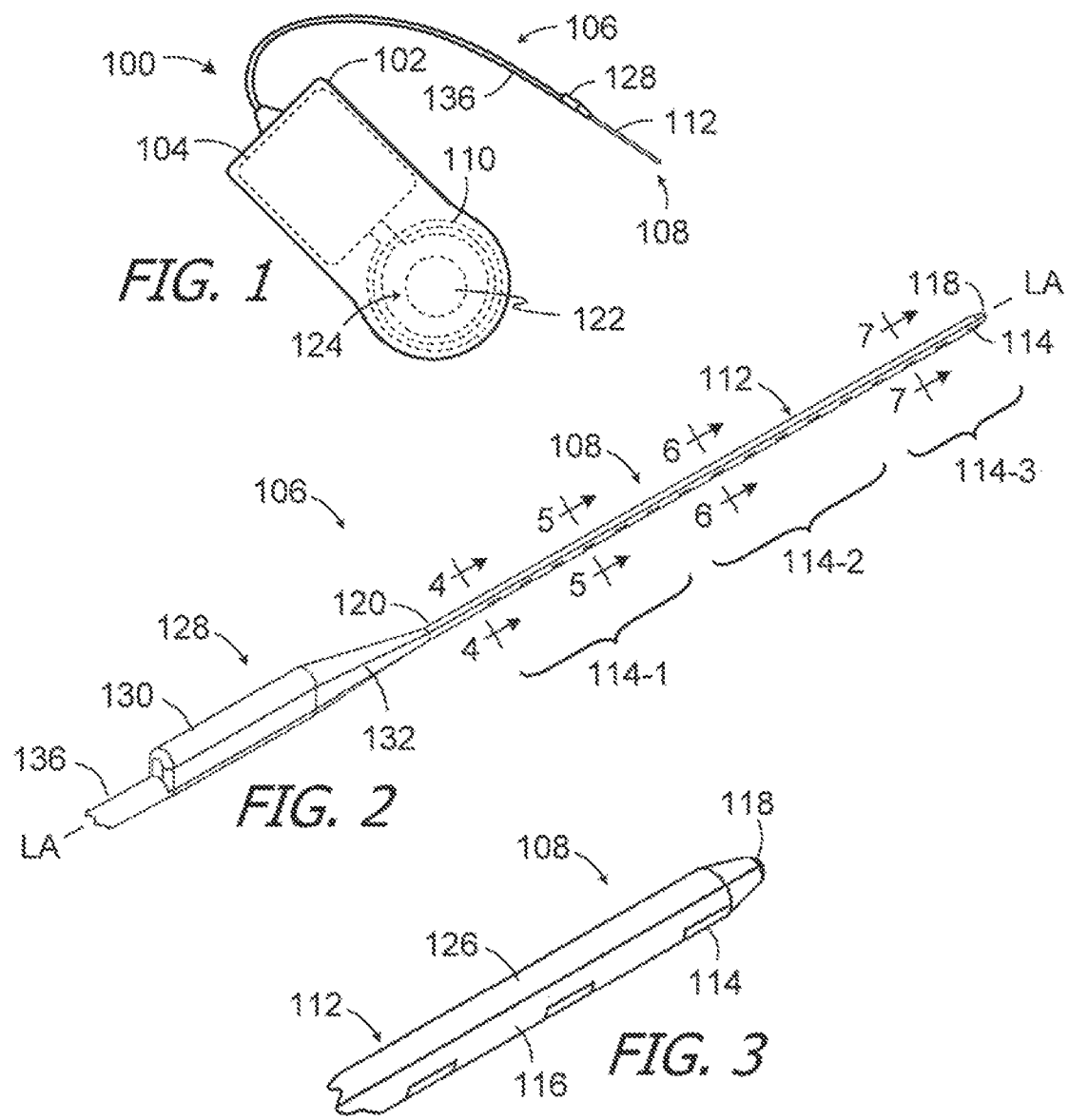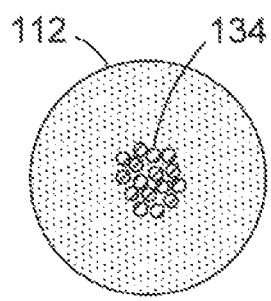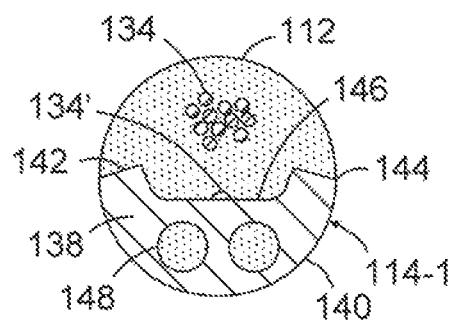

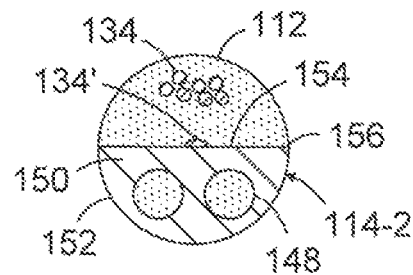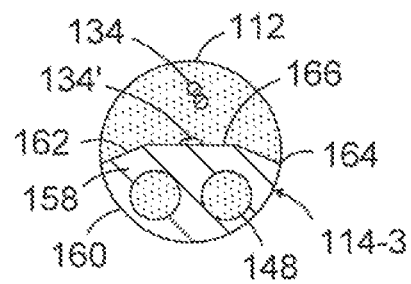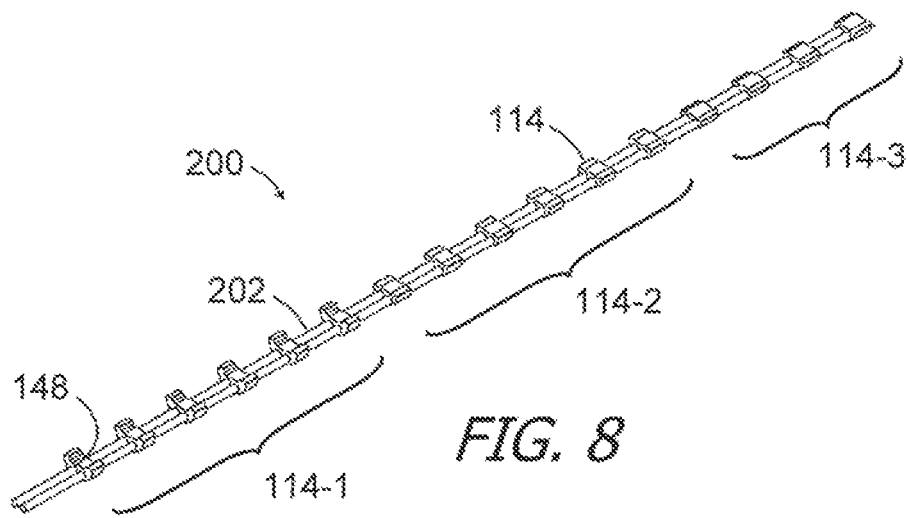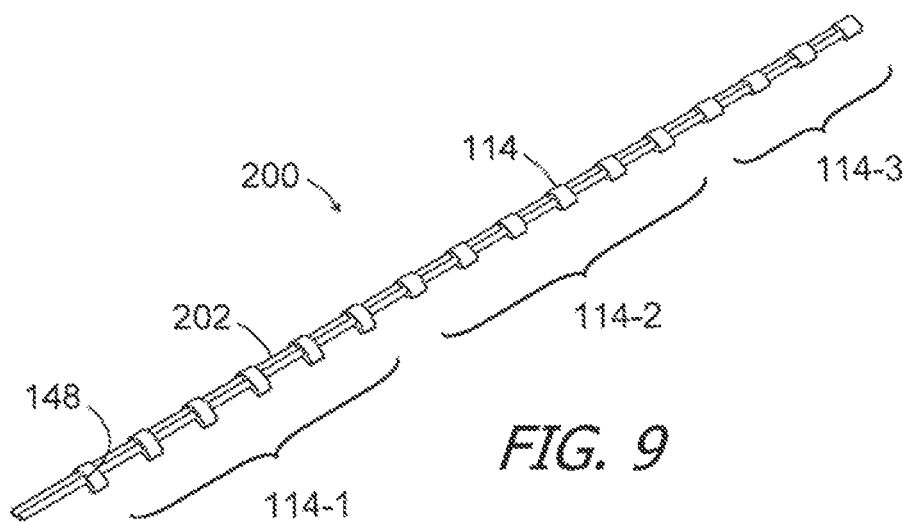

COCHLEAR IMPLANTS INCLUDING ELECTRODE ARRAYS AND METHODS OF MAKING THE SAME

CROSS-REFERENCE TO RELATED APPLICATIONS

This application is a continuation of U.S. App. Ser. No. 16/463,957, filed May 24, 2019, now U.S. Pat. No. 11,123,551, which is the U.S. National Stage of PCT App. Ser. No. PCT/US2017/064231, filed Dec. 1, 2017, which claims priority to U.S. Prov. App. Ser. No. 62/428,668, filed Dec. 1, 2016, which is incorporated herein by reference.

BACKGROUND

1. Field

The present disclosure relates generally to the implantable portion of implantable cochlear stimulation (or "ICS") systems and, in particular, to electrode arrays.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates, and/or amplitudes, and transmitted to an implanted receiver circuit of the ICS system. The implanted receiver circuit is connected to an implantable lead with an electrode array that is inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Harmony™ BTE sound processor, the Naida™ CI Q Series sound processor and the Neptune™ body worn sound processor, which are available from Advanced Bionics.

As alluded to above, some ICS systems include an implantable cochlear stimulator (or "cochlear implant") having a lead with an electrode array, a sound processor unit (e.g., a body worn processor or behind-the-ear processor) that communicates with the cochlear implant, and a microphone that is part of, or is in communication with, the sound processor unit. The cochlear implant electrode array, which is formed by a molding process, includes a flexible body formed from a resilient material such as liquid silicone rubber ("LSR") and a plurality of electrically conductive contacts (e.g., sixteen platinum contacts) spaced along a surface of the flexible body. The contacts of the array are connected to lead wires that extend through the flexible body. Once implanted, the contacts face the modiolus within the cochlea.

The present inventors have determined that conventional methods of manufacturing electrode arrays are susceptive to improvement. The electrically conductive contacts, which must have a clean exposed surface to function properly, are masked during the molding process to prevent the LSR or other resilient material from covering the contacts. In some conventional processes, the contacts are welded to an iron strip and the lead wires are welded to the contacts while they are supported on iron strip. The iron strip masks portions of the contacts. The contacts, iron strip and lead wires are then placed into a mold that is configured to accommodate the iron strip. Resilient material is injected into the mold to form the flexible body of the electrode array through an overmolding process. The electrode array is removed from the mold once the resilient material has cured. The iron strip is then etched away from the contacts, in a bath of nitric acid or hydrochloric acid, thereby exposing the contacts. The contacts must be cleaned after the acid bath. The acid bath and cleaning take approximately 8 hours. The present inventors have determined that it would be desirable to avoid the use of harsh chemicals and the production delay associated therewith. The present inventors have also determined that welded masks can result in an uneven and uncontrolled contact surface, with small granulations in surface structure, which is more likely to experience biofilm and fibrous tissue growth than a smooth surface. Irregular surfaces are also likely to result in electrical impedances that vary from contact to contact. Exemplary methods of manufacturing electrode arrays are disclosed in U.S. Pat. Pub. No. 2011/0016710.

The present inventors have also determined that conventional electrode arrays are susceptive to improvement. For example, conventional electrode arrays can buckle during the insertion process, which necessitates repositioning and can result in damage to any still functioning hair cells in the cochlea that allow residual hearing to occur. In particular, when a thin electrode array (e.g., diameter of about 0.33 mm) that is configured for placement against the lateral wall is inserted into an opening in the cochlea, such as an opening formed by the "round window" technique or a cochleostomy, the base portions of thin electrode arrays sometimes buckle mid-way through the insertion procedure. Exemplary methods of stiffening electrode arrays are disclosed in U.S. Pat. Nos. 8,249,724, 8,812,121, 8,880,193, 9,033,869, 9,037,267, and 9,492,654 and U.S. Pat. Pub. No. 2011/0137393.

The present inventors have determined that conventional methods of making electrode arrays are susceptive to improvement, For example, some conventional methods involve the use of electrode array assemblies that include a plurality of conductive contacts which are respectively connected to a plurality of lead wires, A carrier (or "bridge" formed from a silicone adhesive is then applied to the contacts and lead wires prior to the remainder of the electrode array being molded onto the assembly. One example of a method that involves the use of such a bridge is disclosed in U.S. Pat. Pub. No. 2011/0016710. The present inventors have determined that placing the electrode array subassembly in a curved mold to form the carrier over lead wires can cause the lead wires to break.

SUMMARY

A method of forming a cochlear implant electrode array in accordance with one of the present inventions includes the steps of positioning a contact array assembly, which includes at least one carrier and a plurality of electrically conductive contacts on the at least one carrier, in a mold, removing at least a portion of the at least one carrier from the mold without removing the plurality of electrically conductive contacts from the mold, and introducing resilient material into the mold after the at least one carrier has been removed to form a flexible body.

A contact array assembly for use in during the manufacture of a cochlear implant electrode array in accordance with one of the present inventions includes at least one carrier and a plurality of electrically conductive contacts, which are sized and shaped for insertion into the cochlea, removably mounted on the at least one carrier.

A cochlear implant in accordance with one of the present inventions includes a housing, an antenna within the housing, a stimulation processor, and an electrode array operably connected to the stimulation processor. The electrode array may include a flexible body and a plurality of electrically conductive contacts, with a tissue contact surface and at least one cylindrical aperture, carried on the flexible body such that the tissue contact surfaces are exposed and portions of the flexible body extend through the at least one cylindrical aperture of at least some of the electrically conductive contacts.

A cochlear implant in accordance with one of the present inventions includes a housing, an antenna within the housing, a stimulation processor, and an electrode array operably connected to the stimulation processor. The electrode array may include a flexible body, a plurality of electrically conductive contacts, with a tissue contact surface and a pair of contact connectors, carried on the flexible body such that the tissue contact surfaces are exposed, and at least one relatively stiff, electrically non-conductive link with a pair of link connectors that connects two adjacent contacts to one another. The contact connectors and the link connectors may be respectively configured such that the link connectors can engage with, and disengage from, the contact connectors prior to formation of the flexible body.

A method of forming a cochlear implant electrode array including a flexible body, a plurality of electrically conductive contacts on the flexible body and a plurality of lead wires respectively connected to the plurality of electrically conductive contacts in accordance with one of the present inventions includes the steps of forming a contact array assembly by positioning the electrically conductive contacts and lead wires within a cavity in such a manner that one end of each lead wire is connected to a respective electrically conductive contact and the remainder of each lead wire is located outside of the cavity, and forming a carrier that defines a portion of the flexible body by introducing resilient material into the cavity while the remainder of each lead wire is located outside of the cavity, positioning the contact array assembly in a curved mold with the remainders of the lead wires located outside of the carrier and free to move relative to the carrier, and introducing resilient material into the curved mold to complete the flexible body.

There are a number of advantages associated with such methods and apparatus. For example, removing some or all of the carrier prior to molding eliminates the need for the post-molding etching processes associated with some conventional methods. Also, because the carrier is not associated with (and not in contact with) the tissue contact surfaces of the contacts, the present method and apparatus produce a smooth, clean surface that is less likely to experience biofilm and fibrous tissue grown after implantation or electrical impedances that vary from contact to contact. Keeping the lead wires out of the cavity in which the carrier is formed prevents the carrier from being formed over the lead wires. As a result, the lead wires will be free to move relative the remainder of the electrode array assembly when the electrode array assembly is placed in a curved mold, thereby reducing the likelihood that the lead wires will break.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 1 is a plan view of a cochlear implant in accordance with one embodiment of a present invention.

FIG. 2 is a perspective view of a portion of the cochlear lead illustrated in FIG. 1.

FIG. 3 is a perspective view of a portion of the cochlear lead illustrated in FIG. 1.

FIG. 4 is a section view taken along line 4-4 in FIG. 2.

FIG. 5 is a section view taken along line 5-5 in FIG. 2.

FIG. 6 is a section view taken along line 6-6 in FIG. 2.

FIG. 7 is a section view taken along line 7-7 in FIG. 2.

FIG. 8 is a perspective view of a contact array assembly in accordance with one embodiment of the present invention.

FIG. 9 is another perspective view of the contact array assembly illustrated in FIG. 8.

DETAILED DESCRIPTION OF THE EXEMPLARY EMBODIMENTS

Figure 10:
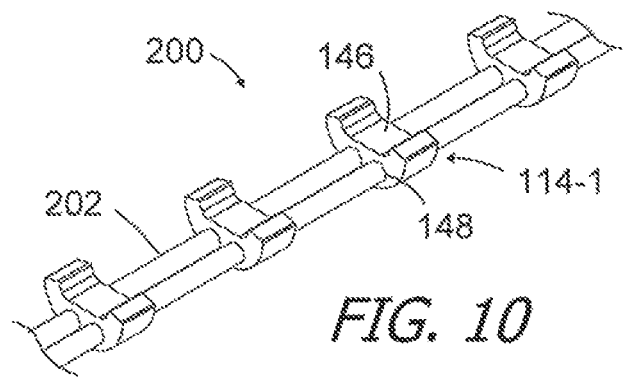
FIG. 10 is a perspective view of a portion of the contact array assembly illustrated in FIG. 8.
Figure 11:
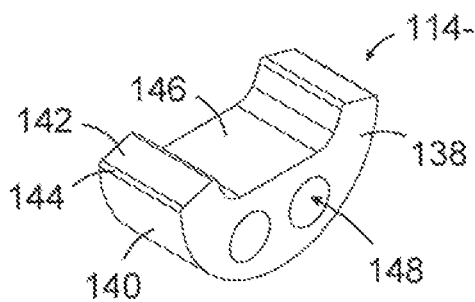
FIG. 11 is a perspective view of one of the contacts in the contact array assembly illustrated in FIG. 8.
Figure 12:
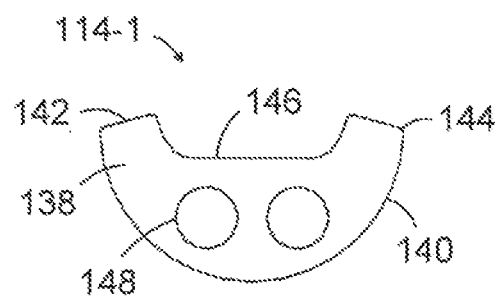
FIG. 12 is an end view of the contact illustrated in FIG. 11.
Figure 13:
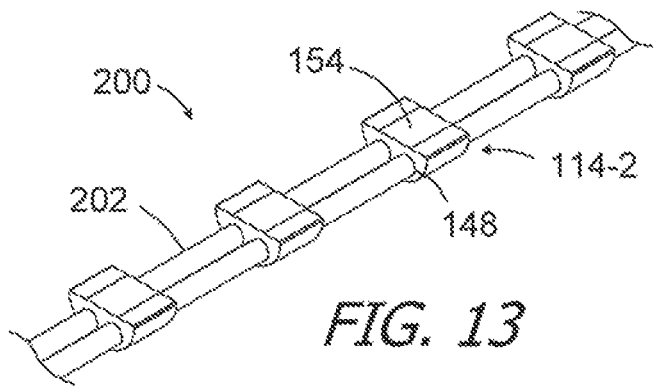
FIG. 13 is a perspective view of a portion of the contact array assembly illustrated in FIG. 8.
Figure 14:
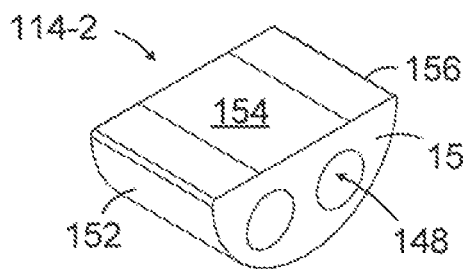
FIG. 14 is a perspective view f one of the contacts in the contact array assembly illustrated in FIG. 8.
Figure 15:
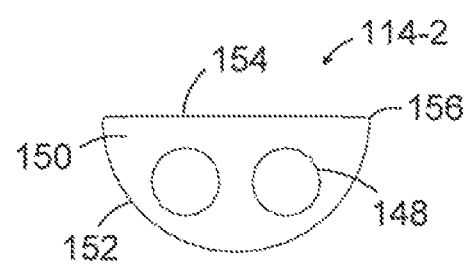
FIG. 15 is an end view of the contact illustrated in FIG. 14.
Figure 16:
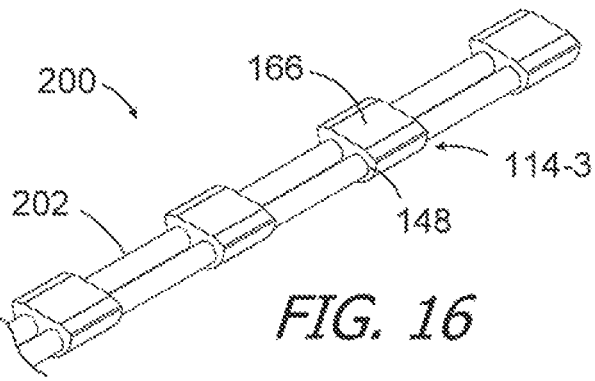
FIG. 16 is a perspective view of a portion of the contact array assembly illustrated in FIG. 8.
Figure 17:
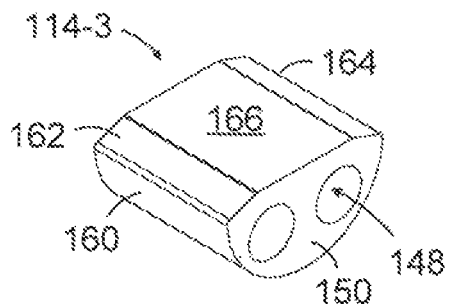
FIG. 17 is a perspective view of one of the contacts in the contact array assembly illustrated in FIG. 8.
Figure 18:
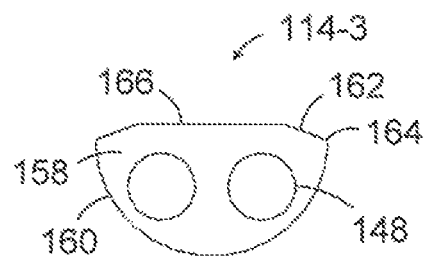
FIG. 18 is an end view of the contact illustrated in FIG. 17.

The following is a detailed description of the best presently known modes of carrying out the inventions. This description is not to be taken in a limiting sense, but is made merely for the purpose of illustrating the general principles of the inventions.

One example of a cochlear implant (or "implantable cochlear stimulator") in accordance with at least some of the present inventions is illustrated in FIGS. 1-7. The cochlear implant 100 includes a flexible housing 102 formed from a silicone elastomer or other suitable material, a processor assembly 104, a cochlear lead 106 with an electrode array 108, and an antenna 110 that may be used to receive data and power by way of an external antenna that is associated with, for example, a sound processor unit. The electrode array 108 includes a flexible body 112 and a plurality of electrically conductive contacts 114 (e.g., the sixteen contacts 114 illustrated in FIG. 2) spaced along the curved bottom surface 116 of the flexible body between the tip 118 and the base 120. A positioning magnet 122 is located within a magnet pocket 124. The magnet 122 is used to maintain the position of a headpiece transmitter over the antenna 110. The cochlear implant may, in some instances, be configured is manner that facilitates magnet removal and replacement. Here, the housing 102 may be provided with a magnet aperture (not shown) that extends from the magnet pocket 124 to the exterior of the housing.

Suitable materials for the flexible body 112 include, but are not limited to, LSR, high temperature vulcanization ("HTV") silicone rubbers, room temperature vulcanization ("RTV") silicone rubbers, and thermoplastic elastomers ("TPEs"). The contacts 114 may be referred to in numbered order, $1^{st}$ through $16^{th}$, with the contact closest to the tip 118 being the $1^{st}$ contact and the contact closest to the base 120 being the $16^{th}$ contact. The exemplary flexible body 112 also includes a longitudinally extending curved top surface 126 that does not include conductive contacts. Once implanted, the conductive contacts 114 on the curved surface 116 face the modiolus within the cochlea. The exemplary flexible body 112 has a circular shape in a cross-section perpendicular to the longitudinal axis LA of the electrode array 108 (FIGS. 4-7). In other implementations, a truncated circular shape, with a flat top surface, or an oval shape, with or without truncation, or any other suitable shape, may be employed. It should also be noted that the methods of forming the electrode array described below produce smooth exterior surface transitions from the flexible body 112 to the contacts 114.

Referring more specifically to FIG. 2, in addition to the electrode array 108, the exemplary cochlear lead 106 includes a wing 128, with a rectangular portion 130 and a tapered portion 132, which functions as a handle for the surgeon during the implantation surgery. The wing 128 also provides tension relief for lead wires 134 (FIG. 4), which do not run straight through the wing. A tubular member 136, which may consist of tubes of different sizes, extends from the wing 128 to the housing 102. The contacts 114 are connected to the lead wires 134 that extend through the flexible body 112 and tubular member 136 to a connector (not shown) in the housing 102.

The exemplary electrode array 108 has a tapered shape, with a diameter that is larger at the base 120 than at the tip 118, and includes contacts 114 of different sizes and shapes. In the illustrated embodiment, there are three different contact configurations, i.e., contacts 114-1, 114-2 and 114-3, and reference numeral 114 is used herein to refer to all of the contacts generically. Contacts 114-1 (and the associated portion of the flexible body 112) are larger than contacts 114-2 (and the associated portion of the flexible body), and contacts 114-2 (and the associated portion of the flexible body) are larger than contacts 114-3 (and the associated portion of the flexible body).

As illustrated in FIGS. 5 and 10-12, the exemplary contacts 114-1 include a solid body 138, a curved tissue contact surface 140, side surfaces 142 with outer edges 144, and a flat wire contact surface 146. One or more apertures 148 (two cylindrical apertures in the illustrated implementation) extend through the solid body 138. The apertures 148 are located inward of, and are offset from, the tissue contact surface 140. Prior to the molding process, the apertures 148 support the contacts 114-1 on carrier rods 202, as is discussed below with reference to FIGS. 8 and 9. The carrier rods 202 are removed prior to the molding process used in the formation of the electrode array 108. As a result, portions of the flexible body 112 are located within the apertures 148, thereby interlocking the contacts 114-1 with the flexible body. As discussed below with reference to FIGS. 19-21, one of the wires 134 is connected to the wire contact surface 146 at a bond 134'. Turning to FIGS. 6 and 13-15, the exemplary contacts 114-2 include a solid body 150, a curved tissue contact surface 152, and a flat wire contact surface 154 with outer edges 156. One or more apertures 148 (two in the illustrated implementation) extend through the solid body 150. The apertures 148 are located inward of, and are offset from, the tissue contact surface 152. One of the wires 134 is connected to the wire contact surface 146 at a bond 134'. The exemplary contacts 114-3 (FIGS. 7 and 16-18) include a solid body 158, a curved tissue contact surface 160, side surfaces 162 with outer edges 164, and a flat wire contact surface 166. One or more apertures 148 (two in the illustrated implementation) extend through the solid body 158. The apertures 148 are located inward of, and are offset from, the tissue contact surface 160. One of the wires 134 is connected to the wire contact surface 166 at a bond 134'.

Suitable conductive materials for the contacts 114 include, but are not limited to, platinum, platinum-iridium, gold and palladium. The exemplary contacts 114 may be solid (as shown) or a PEEK or ceramic structure that is coated or plated with the conductive material. With respect to dimensions, the exemplary contacts 114 are sized and shaped for insertion into the cochlea and have widths (measured horizontally in FIGS. 5-7) that range from 0.35 mm to 0.5 mm, and radii that range from 0.17 mm to 0.25 mm. The exemplary apertures 148 are circular in cross-section with diameters that range from 0.1 mm to 0.15 mm. The distance between adjacent contacts 114 may range from 0.5 mm to 1.5 mm, and the distance may be constant or variable. It should also be noted that the contacts 114 have the same configuration before and after being placed onto the carrier rods 202 (discussed below).

Contacts such as contacts 114 may form part of a contact array assembly that is used during the formation of an electrode array. In the exemplary contact array assembly 200 illustrated in FIGS. 8 and 9, which is used in the formation of the electrode array 108, all three types of contacts 114 (i.e., contacts 114-1, 114-2 and 114-3) are positioned on carrier rods 202 that extend through the contact apertures 148. The carrier rods 202 are located inward of, and are offset from, the tissue contact surfaces 140, 152 and 160 of the contacts 114-1, 114-2 and 114-3. A slip fit, a line to line fit, or a slight friction fit between the contacts 114 and the carrier rods 202 allows the carrier rods to be separated from the contacts at the appropriate time (e.g., after the contact array assembly has been placed in a mold) without destroying the carrier rods and/or the contacts or altering the spacing between adjacent contacts. In some instances, instead of a slight friction fit, a small amount of medical grade adhesive may be used to fix the positions of the contacts 114 on the carrier rods 202 with bonds that are weak enough to allow the carrier rods to be separated from the contacts. Put another way, in the illustrated implementation, the carrier rods 202 are removably inserted into apertures 148 of the contacts 114.

Figure 28:
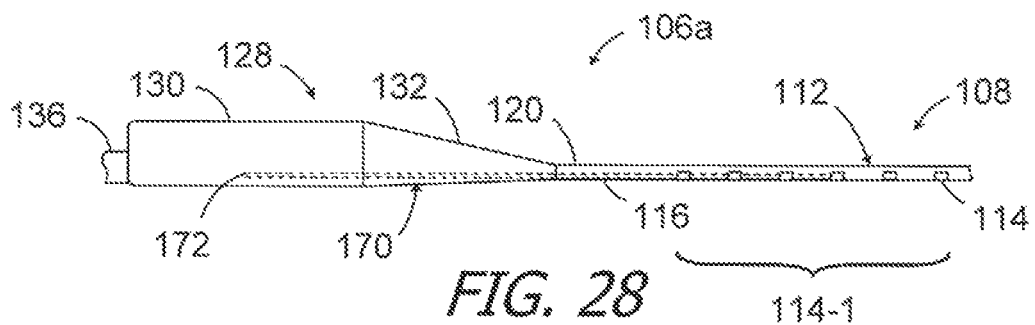
FIG. 28 is a side view of a portion of the cochlear lead in accordance with one embodiment of a present invention.

The exemplary carrier rods 202 are malleable, which allows the contact array assembly 200 to be bent in order to conform to curved molds that produce pre-curved electrode arrays. Suitable structures for the carrier rods 202 include, but are not limited to, stainless steel rods (e.g., gauge pins) with a diameter of 0.1 mm to 0.15 mm. In other implementations, the carrier rods may be resilient (i.e., will bend and then return to their original shape when the bending force is removed), super-elastic, or rigid. In other implementations, such as that described below with reference to FIGS. 28-30, the carrier rods 202 may be formed from electrically non-conductive material such as PEEK, PTFE or polyester, as well as the shape memory materials described below.

It should also be noted here that the present contact array assemblies are not limited to the exemplary assembly 200. For example, other implementations may include fewer than (or more than) sixteen contacts and/or contacts that all have the same configuration. Other exemplary contact array assemblies are described below with reference to FIGS. 31-75.

Figure 19:
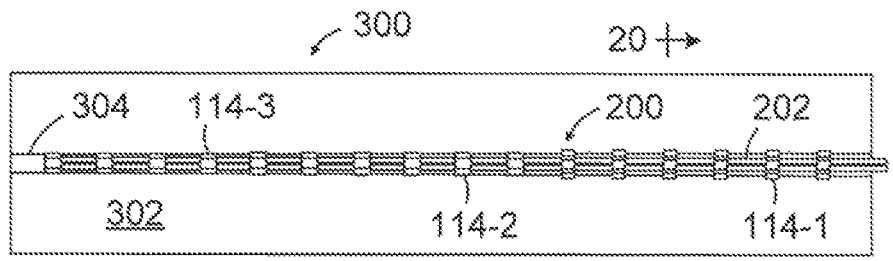
FIG. 19 is a plan view of the contact array assembly illustrated in FIG. 8 on a wire bonding fixture.
Figure 20:
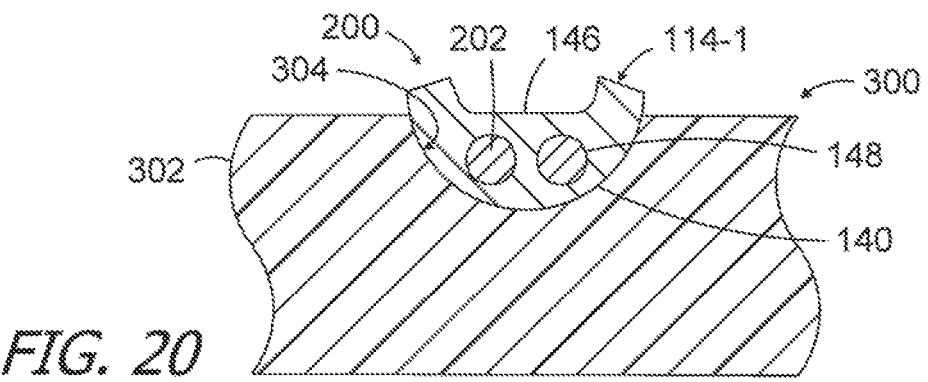
FIG. 20 is a section view taken along line 20-20 in FIG. 19.
Figure 21:
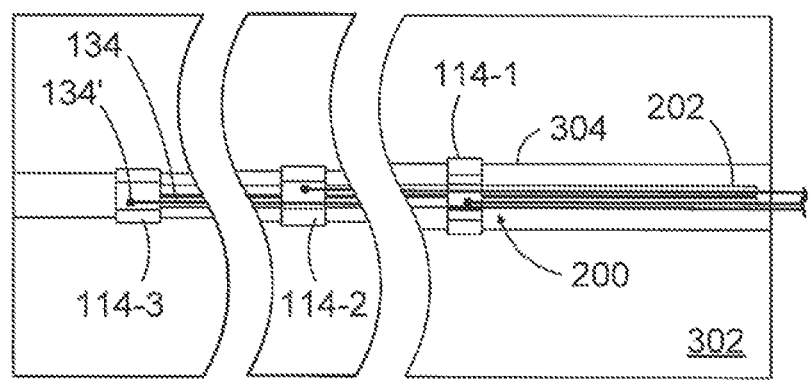
FIG. 21 is a plan view of the contact array assembly illustrated in FIG. 19 with wires bonded thereto.

As illustrated for example in FIGS. 19 and 20, the contact array assembly 200 may be positioned on a wire bonding fixture 300 that holds the contact array assembly while the lead wires 134 are being bonded to the individual contacts 114. The exemplary bonding fixture 300 includes a main body 302 and a channel 304 that is sized and shaped to accommodate the contacts 114. Individual pockets (not shown) or other suitable structures may be provided within the channel 304 to insure that the electrodes 114 are properly spaced. After the contact array assembly 200 has been positioned on the wire bonding fixture 300, each lead wire 134 (sixteen in the illustrated implementation) may be physically bonded and electrically connected to a respective one of the wire contact surfaces 146, 154 and 166 of the contacts 114-1, 114-2 and 114-3 in the manner illustrated in FIG. 21 (where only three lead wires are shown for purposes of clarity). For example, the end portion of each lead wire 134 may be stripped of insulation and bonded to the wire contact surface 146 (or 154 or 166) by resistance welding, wire bonding, hot bar welding, or any other suitable technique to form the bonds 134'. The bonds 134' may be created in series, starting with contact sixteen (i.e., the contact 114-1 that will be closest to the base 120) and ending with contact one (i.e. the contact 114-3 that will be closest to the tip 118), to prevent damage to the lead wires 134. The resulting lead wire bundle may be secured to the some or most of the contacts 114 with medical grade adhesive. The stiffness of the lead wires 134 helps maintain proper spacing between the contacts 114.

Figure 22:
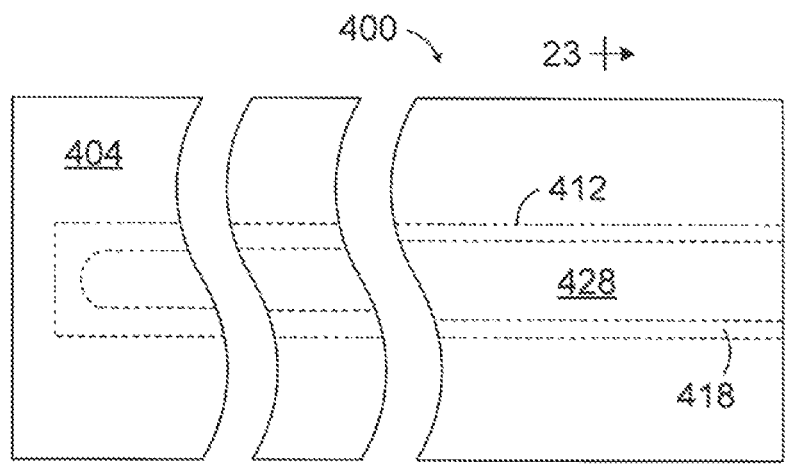
FIG. 22 is a plan view of a mold in accordance with one embodiment of a present invention.
Figure 23:
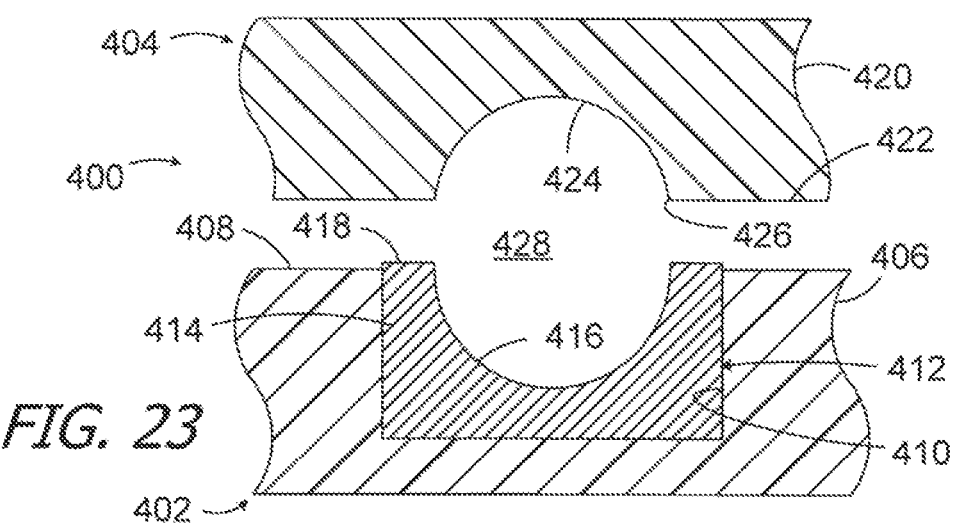
FIG. 23 is an exploded section view taken along line 23-23 in FIG. 22.

The contact array assembly 200, with wires 134 attached thereto, may thereafter be transferred to a mold into which the LSR (or other resilient material) will be injected to form the flexible body 112. One example of such a mold is the mold 400 illustrated in FIGS. 22-27. Referring first to FIGS. 22 and 23, the exemplary mold 400 includes first and second mold parts 402 and 404. The first mold part 402 includes a plate 406 with a contact surface 408 and an elongate cavity 410. A resilient insert 412, which includes a body 414, a curved lead defining surface 416 and top ends 418 that extend beyond the contact surface 408 of the first mold part 402 (e.g., by 0.002 inch), may be positioned within the elongate cavity 410. Suitable materials for the resilient insert include, but are not limited to, urethane, silicone, or any other suitable compliant material. The first mold part 402 and/or the resilient insert 412 may include verification indicia (not shown) so that, prior to molding, the spacing between the contacts 114 can be verified and, if necessary, adjusted. The second mold part 404 includes a plate 420 with a contact surface 422, a curved lead defining surface 424 and edges 426 where the contact surface and channel intersect. After insertion of the contact array assembly 200, and prior to injection of the LSR (or other resilient material), the first and second mold parts 402 and 404 may be clamped together with the lead defining surface 416 aligned with the lead defining surface 424, which together define a mold cavity 428 the shape of the flexible body 112. The top ends 418 are compressed to form a tight seal.

In the illustrated implementation, the mold parts 402 and 404 are intended to be reusable. Suitable materials for the mold plates 406 and 420 include, but are not limited to, stainless steel (e.g., 400 series stainless steel). The resilient insert 412 may be replaced as necessary. In other implementations, the mold may be a single-use device.

Figure 24:
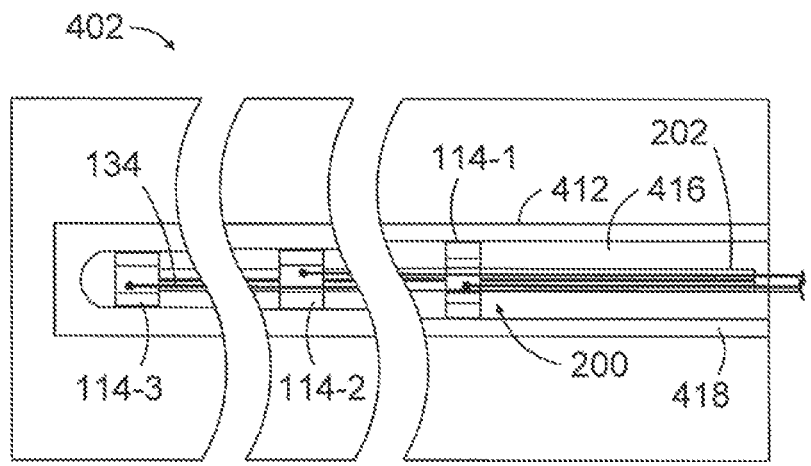
FIG. 24 is a plan view of the contact array assembly illustrated in FIG. 8 on a portion of the mold illustrated in FIGS. 22 and 23 with wires bonded thereto.
Figure 25:
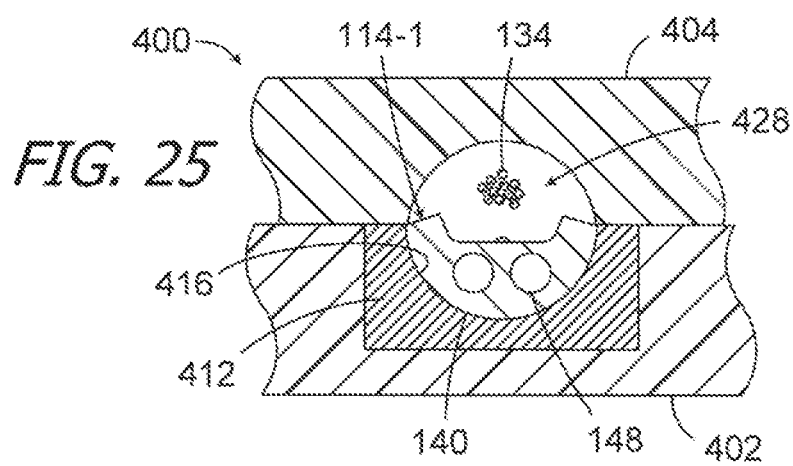
FIG. 25 is a section view showing a portion of the contact array assembly illustrated in FIG. 8 on a portion of the mold illustrated in FIGS. 22 and 23 with wires bonded thereto.
Figure 26:
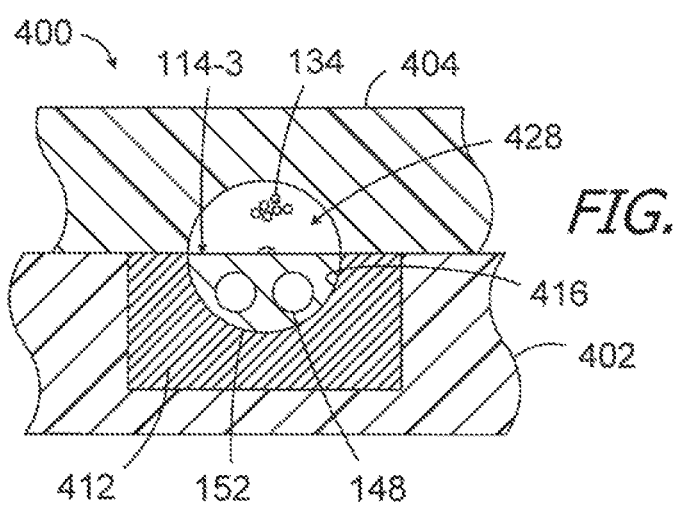
FIG. 26 is a section view showing a portion of the contact array assembly illustrated in FIG. 8 on a portion of the mold illustrated in FIGS. 22 and 23 with wires bonded thereto.
Figure 27:
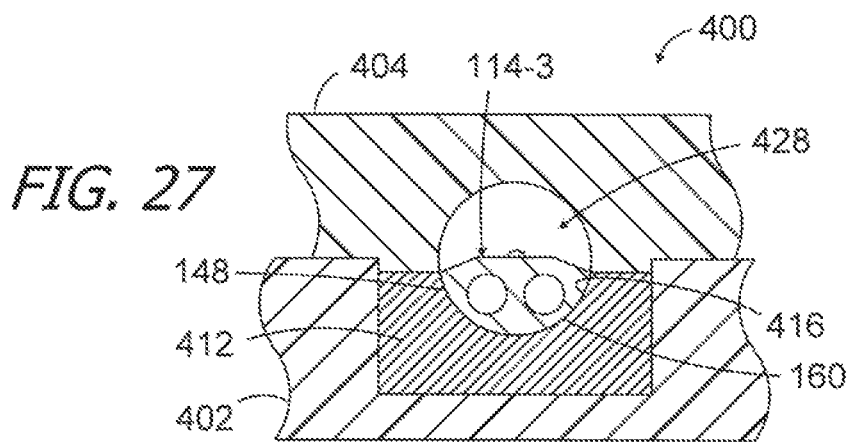
FIG. 27 is a section view showing a portion of the contact array assembly illustrated in FIG. 8 in a mold with wires bonded thereto.

Turning to FIG. 24, the contact array assembly 200, with wires 134 attached thereto, may be pressed into the lead defining surface 416 of the resilient insert 412 while the first and second mold parts 402 and 404 are separated. The resilience of the insert 412 insures that there is a tight fit between the contacts 114 and the lead defining surface 416. The masking effect of the tight fit prevents the LSR (or other resilient material) from flashing over the outer surfaces of the contacts 114 during the injection molding process. The first and second mold parts 402 and 404 may then be brought together and secured to one another, with the surfaces 408 and 422 (FIG. 23) contacting one another and the mold part edges 426 engaging the edges 144, 156 and 164 (FIGS. 5-7) of the contacts 114-1, 114-2 and 114-3 to press the tissue contact surfaces 140, 152, 160 against the lead defining surface 416. The carrier rods 202 may then be pulled out of the contacts 114, which leaves the apertures 148 open in the manner illustrated in FIGS. 25-27. A clamp, screws or other suitable instrumentality (not shown) may be used to hold the mold parts 402 and 404 together. The tight fit between the contacts 114 and the lead defining surface 416 also prevents the contacts from moving when the carrier rods 202 are pulled out.

It should also be noted that the wing 128 (FIG. 2) may in some instances be formed with a mold (not shown) which has a wing-shaped cavity and is aligned with the mold 400 during the injection process.

The LSR or other suitable resilient material may then be injected (or otherwise introduced) into the mold cavity 428, both around the contacts 114 and into the apertures 148, to form the flexible body 112. The masking effect of the lead defining surface 416 prevents the resilient material from flashing over the outer surfaces of the contacts 114. The resilient material within the apertures 148 (FIGS. 5-7) creates a mechanical interlock between the flexible body 112 and the contacts 114. After the resilient material hardens, the mold parts 402 and 404 may be separated from one another. The completed electrode array 108 may be removed from the insert 412 by, for example, simply pulling the completed flexible body 112 out of the insert.

There are some instances where it may be desirable to increase the stiffness of the electrode array in the region adjacent to the wing to, for example, prevent the electrode array from buckling during the insertion process. One example of a cochlear lead that includes such an increase in stiffness is the cochlear lead 106a illustrated in FIGS. 28 and 29. The cochlear lead 106a is substantially similar to the cochlear lead 106 described above with reference to FIGS. 1-18. For example, the cochlear lead 106a includes an electrode array 108 with a flexible body 112 and a plurality of electrically conductive contacts 114 (e.g., the sixteen contacts 114 illustrated in FIG. 2) between the tip and the base 120 that are connected to lead wires in the manner described above. A wing 128, with a rectangular portion 130 and a tapered portion 132, is located at the electrode array base 120. The cochlear lead 106a may also be incorporated into the cochlear implant 100 in place of the lead 106.

Here, however, the lead 106a also includes a stiffener 170 that extends through a plurality of the contacts 114, through the base 120, and into the wing 128. The stiffener 170 has a first end 172 that is located within the rectangular portion 130 of the wing 128 and a second end 174 that is located within one of the contacts 114.

Figure 29:
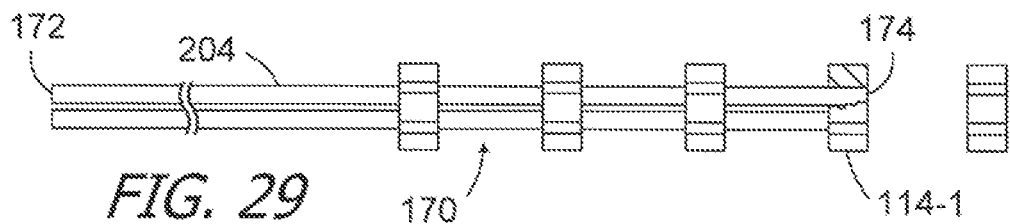
FIG. 29 is a plan view of a portion of a contact array assembly in accordance with one embodiment of the present invention.
Figure 30:
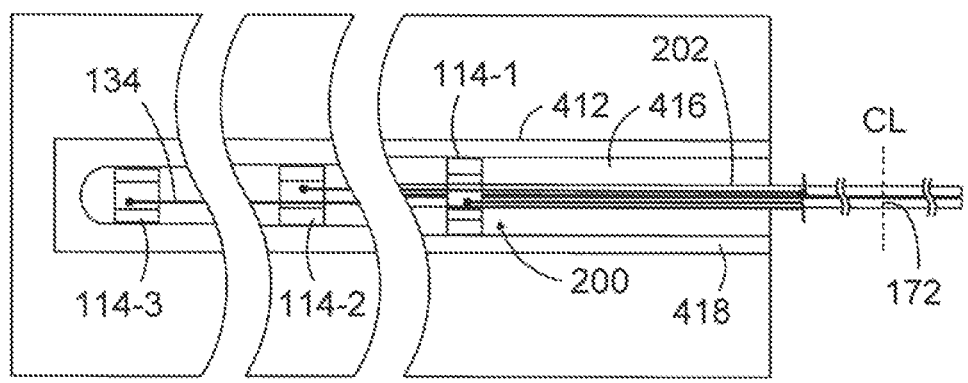
FIG. 30 is a plan view of the contact array assembly illustrated in FIG. 29 on a portion of the mold illustrated in FIGS. 22 and 23 with wires bonded thereto.

In the illustrated implementation, the stiffener 170 is formed from portions 204 of the carrier rods 202 in the contact array assembly 200. Instead of pulling the carrier rods 202 out of each of contacts 114-1, 114-2 and 114-3 when the electrode array assembly is on the mold part 402, as is described above with reference to FIGS. 24-27, the carrier rods are pulled until they only remain in those contacts 114 through which the stiffener 170 is intended to extend. Referring to FIG. 30, once the ends of the carrier rods 202 are aligned with only the intended contacts 114 (e.g., the four contacts 114-1 closest to the wing 128), the carrier rods may be cut or otherwise severed along a cut line CL to form the rod portions 204 (FIG. 29). The cut line CL may be located at the portion of the carrier rods 202 that will define the first end 172 of the stiffener 170. The flexible body 112 may then be molded onto the contacts 114 in the manner described above. It should also be noted that the rods 202 use to form the stiffener 170 are electrically non-conductive.

It should also be noted that in those instances where portions of the carrier rods are used to form a stiffener that remains in a contact array assembly, one rod or more than two rods may be employed, and cross-sectional shapes other than circular may be employed to provide desired bending characteristics. By way of example, by not limitations, one or more carrier rods with oval, rectangular, octagon, 1-beam, or other shapes may be employed.

Figure 31:
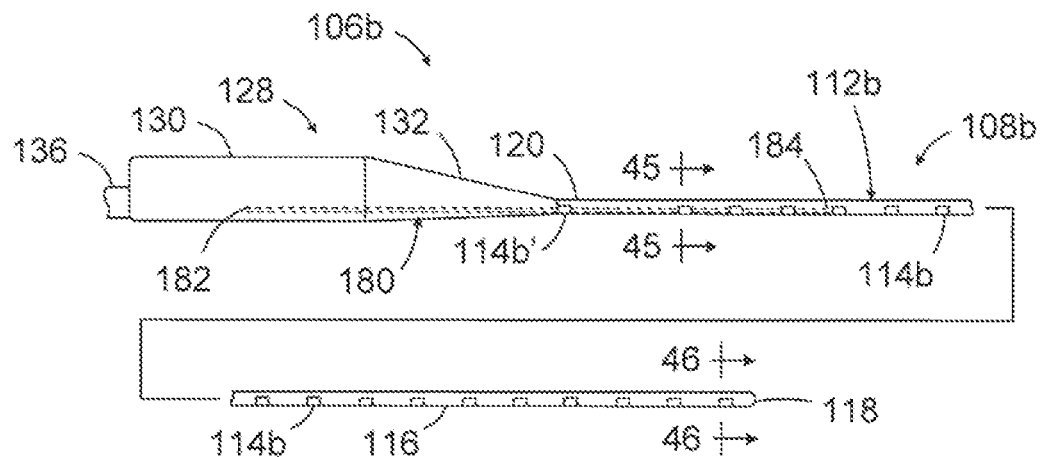
FIG. 31 is a side view of a portion of cochlear lead in accordance with one embodiment of a present invention.

Another exemplary cochlear lead that includes an increase in stiffness adjacent to the wing 128 is the cochlear lead 106b illustrated in FIG. 31. The cochlear lead 106b is substantially similar to the cochlear lead 106a described above with reference to FIGS. 28-30. The cochlear lead 106b, which may also be incorporated into the cochlear implant 100 in place of the lead 106, includes an electrode array 108b with a flexible body 112b and a plurality of electrically conductive contacts 114b (e.g., the sixteen contacts 114b illustrated in FIG. 32) between the tip 118 and the base 120 that are connected to lead wires in the manner described below. Contact sixteen is closest to the base 120 and contact one is closest to the tip 118. A wing 128, with a rectangular portion 130 and a tapered portion 132, is located at the electrode array base 120. A stiffener 180 is associated with a plurality of the contacts 114b that are adjacent to the base 120. The stiffener 180 also extends into the wing 128, and has a first end 182 that is located within the rectangular portion 130 of the wing 128 and a second end 184 that is located within the flexible body 120. The stiffener 180 may be formed from portions of a contact array assembly 200b (FIGS. 32-34) that is used in the manufacturing process. In some instances, the end portion of the base 120 may include a reinforcement 114b' which, in the illustrated implementation, is an electrically conductive contact that is identical to contacts 114b and is not connected to a lead wire. Other types of reinforcements may also be provided.

Figure 32:
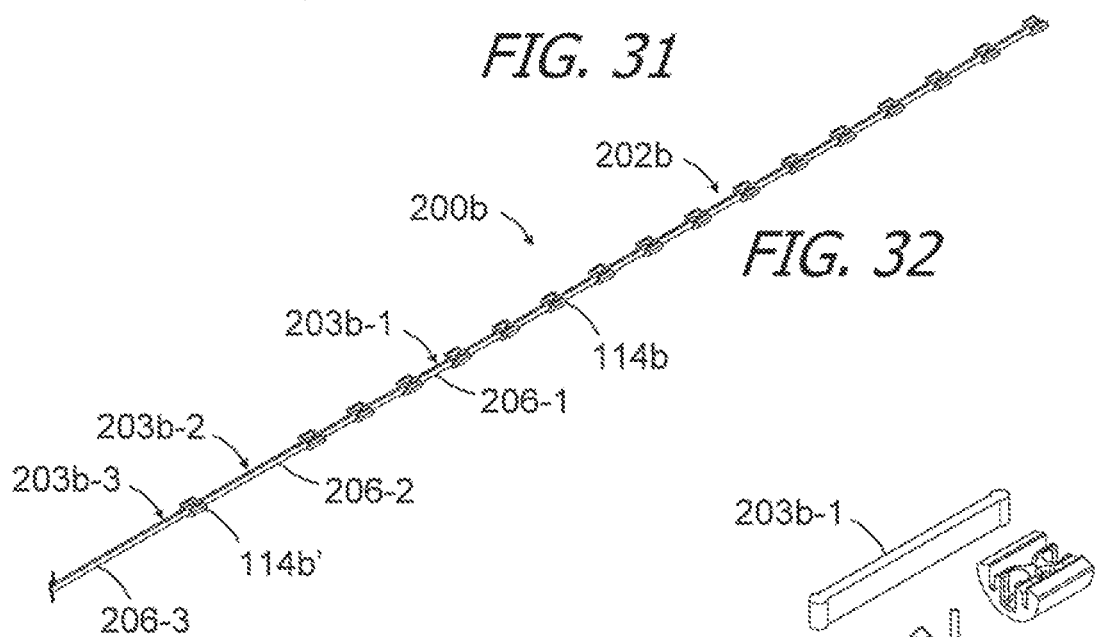
FIG. 32 is a perspective view of a contact array assembly in accordance with one embodiment of the present invention.
Figure 33:
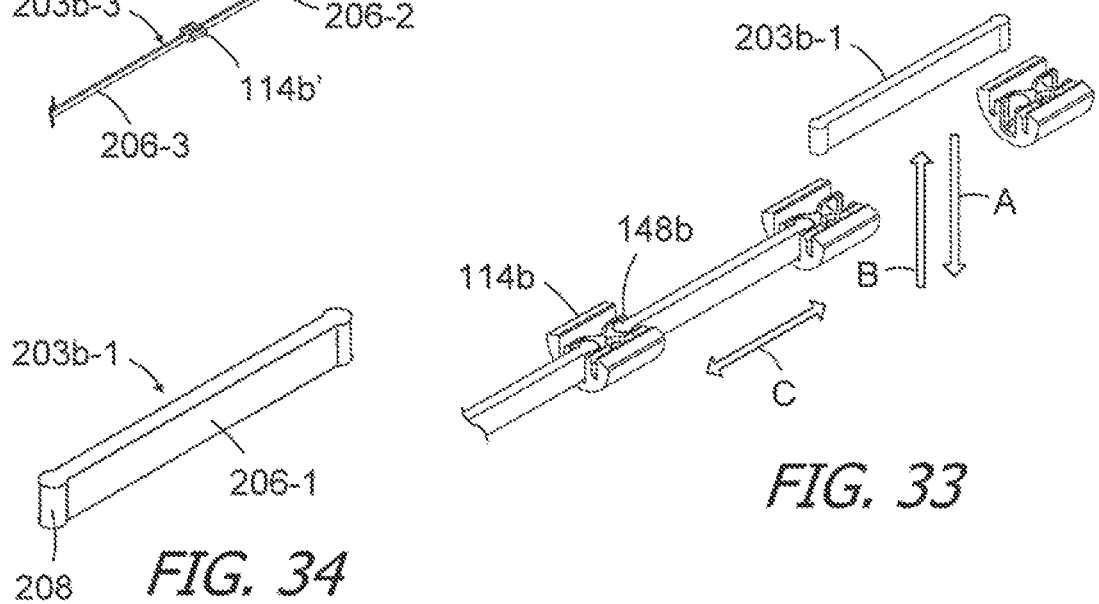
FIG. 33 is an exploded perspective view of a portion of the contact array assembly illustrated in FIG. 32.
Figure 34:
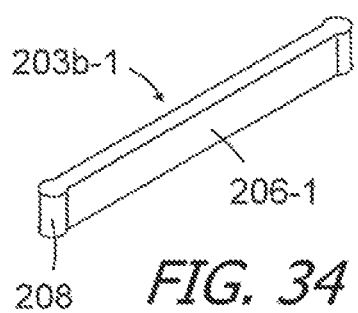
FIG. 34 is a perspective view of a portion of the contact array assembly illustrated in FIG. 32.
Figure 35:
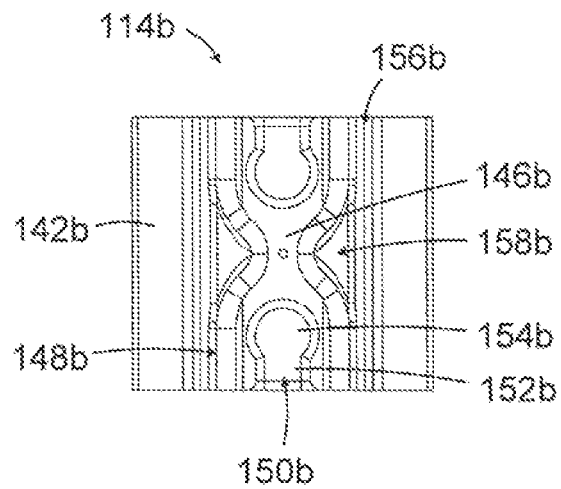
FIG. 35 is a plan view of one of the contacts in the contact array assembly illustrated in FIG. 32.
Figure 36:
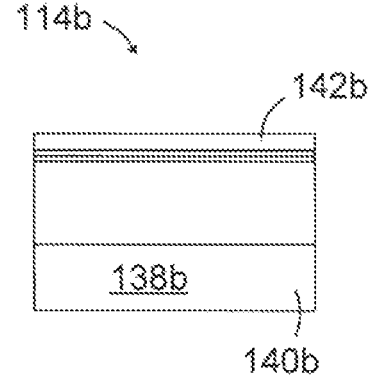
FIG. 36 is a side view of the contact illustrated in FIG. 35.
Figure 37:
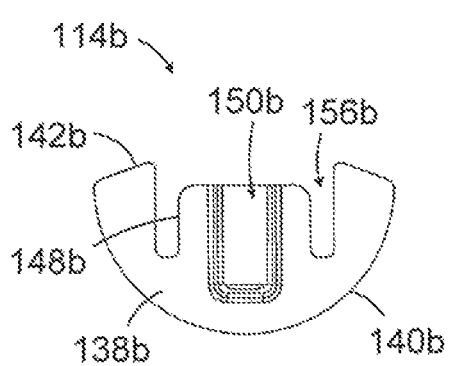
FIG. 37 is an end view of the contact illustrated in FIG. 35.
Figure 38:
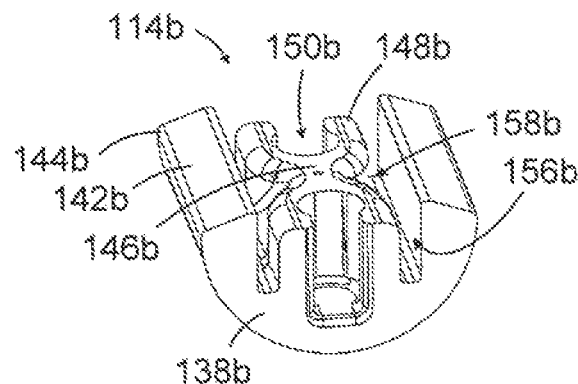
FIG. 38 is a perspective view of the contact illustrated in FIG. 35.

Turning to FIGS. 32-34, the exemplary contact array assembly 200b includes the aforementioned plurality of electrically conductive contacts 114b as well as a carrier 202b that is defined by a plurality of relatively stiff, electrically non-conductive links 203b. As used herein, a relatively stiff link is a link that is formed from material that is stiffer than the LSR (or other resilient material) that is used to form the flexible body 112b. In the illustrated embodiment, there are three different link configurations, i.e., links 203b-1, 203b-2 and 203b-3, and reference numeral 203b is used herein to refer to all of the links generically. The links 203b-1, 203b-2 and 203b-3 include respective rods 206-1, 206-2 and 206-3 as well as connectors 208 located at the longitudinal ends of the rods. The connectors 208 are configured to engage with, and disengage from, corresponding connectors 148b on the contacts 114b when the links 203b are moved in the directions of arrows A and B (FIG. 33). The connectors 208 will not, however, disengage from the corresponding connectors 148b when the contacts 114b are moved in the direction of arrow C. Some of the links 203b will be removed from the assembly 200b prior to the molding of the flexible body 112b as is described below. The links 203b are identical to one another but for the length of the rods 206-1, 206-2 and 206-3 in the illustrated implementation, but may be different in other implementations. The length of the rods 206-1 corresponds to the distance between adjacent contacts 114b. The length of the rod 206-2, which is greater than the length of the rods 206-1, corresponds to the distance between the basal-most contact 114 and the reinforcement 114b'. The length of the rod 206-3, which is greater than the length of the rod 206-2, corresponds to the distance that the stiffener 180 extends into the wing 128.

The relatively stiff, electrically non-conductive links 203b may be formed from material that is 1 to 1000% stiffer than the material used to form the flexible body 112. Suitable materials for the links 203b include, but are not limited to high durometer LSR, PEEK, PTFE and polyester. Shape memory materials may also be employed. For example, the links may straight at room temperature (about 22 C) and curved at body temperature (about 37 C). Suitable shape memory materials include shape memory metals such as Nitinol (with an electrically non-conductive coating such as PTFE or parylene) and shape memory polymers such as polyethylene glycol (PEG). The shape memory links may be used to, for example, create an electrode array that conforms to the shape of the cochlea in a manner similar to a pre-curved electrode array. Such an electrode array provides certain advantages associated with pre-curved electrode arrays that are molded in a curved state, e.g., the ability to position some or all contacts closer to the modiolus, which can be useful in preventing cross-stimulation that occurs when two contacts stimulate the same part of modiolus, without sacrificing certain advantages associated with electrode arrays that are molded in a straight state, e.g., a relatively simple molding process.

The cross-sectional shape of the rods 206-1, 206-2 and 206-3 may be rectangular, as shown. Other cross-sectional shapes, such as I-beam, circular, oval, or hexagon, may be employed to provide different bending characteristics. The connectors 208 are cylindrical, with a diameter larger than the width of the associated rod, in the illustrated implementation so as to correspond to the shape of the contact connectors 148b. Other shapes may also be employed.

Referring to FIGS. 35-38, the exemplary electrically conductive contacts 114b include a solid body 138b, a curved tissue contact surface 140b, side surfaces 142b with outer edges 144b, and a wire contact surface 146b. The connectors 148b are located inward of, and are offset from, the tissue contact surface 140b (as shown). As a result, the links 203b are also located inward of, and are offset from, the tissue contact surface 140b. The connectors 148b also have configurations which correspond to those of the connectors 208. To that end, the exemplary connectors 148b include a slot 150b having a relatively narrow portion 152b and a relatively wide portion 154b. The relatively narrow portion 152b has a rectangular shape while the relatively wide portion 154b has a circular shape. Other connector configurations that allow the contacts 114b and links 203b to be selectively connected and disconnected in the manner described above may be employed.

The respective configurations of the connectors 148b and 208 avow a portion of the carrier 202b (e.g., some of the links 203b-1) to be separated from the contacts 114b at the appropriate time (e.g., after the contact array assembly has been placed in a mold) without destroying the links and/or the contacts or altering the spacing between adjacent contacts. Put another way, in the illustrated implementation, the links 203b-1 are removably secured to the contacts 114b.

Figure 40:
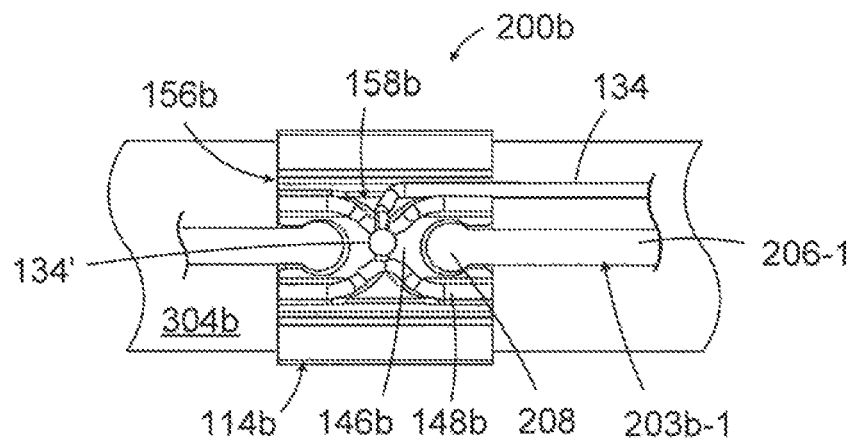
FIG. 40 is a plan view of a portion of the contact array assembly illustrated in FIG. 32 on the wire bonding fixture illustrated in FIG. 39.
Figure 41:
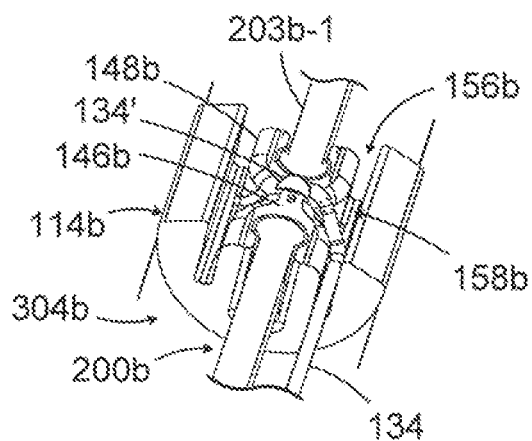
FIG. 41 is a perspective view of a portion of the contact array assembly illustrated in FIG. 32 on the wire bonding fixture illustrated in FIG. 39.
Figure 42:
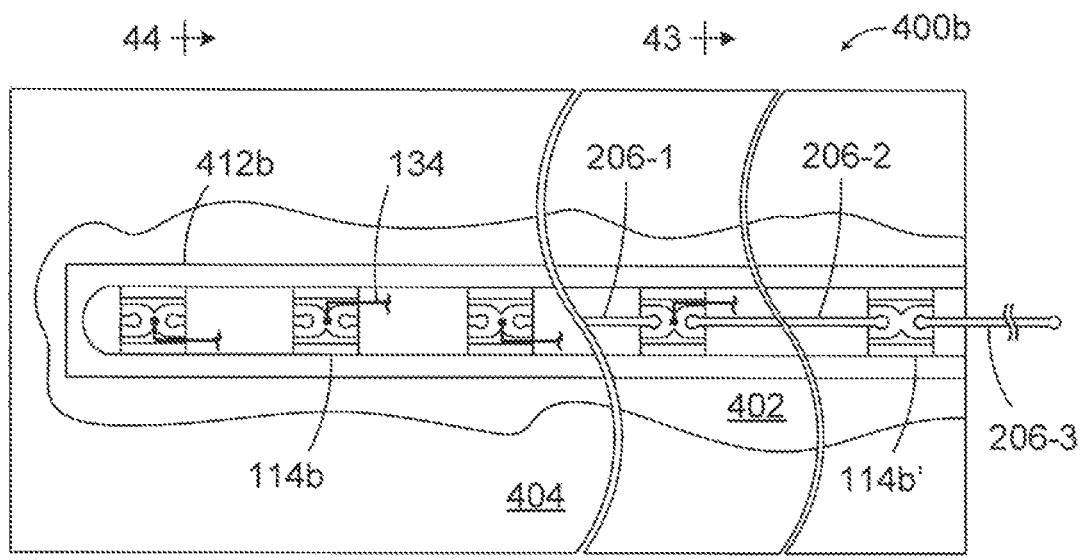
FIG. 42 is a plan, cutaway view of the contact array assembly illustrated in FIG. 32 in a mold with wires bonded thereto.

The exemplary contacts 114b may also be provided with various features that facilitate connection to a lead wire in the manner described below with reference to FIGS. 40 and 41. In the illustrated embodiment, the contacts 114b include a pair of slots 156b that extend from one longitudinal end to the other on opposite sides of the connectors 148b as well as a pair of indentations 158b between the slots and the wire contact surface 146b.

The exemplary contacts 114b may be formed from the conductive materials described above in the context of contacts 114, i.e., materials such as platinum, platinum-iridium, gold and palladium. Suitable manufacturing processes include, but are not limited to, 3-dimensional photo-etching processes such as #D printing, selective laser sintering (SLS), LIGA lithography, electroplating and metal injection molding (MIM) processes. The size and spacing of the contacts 114b may be the same the contacts 114. The contacts 114b may all be the same size (as shown) or may vary in size in those instances where the electrode array 108b has a tapered shape, with an array diameter that is larger at the base 120 than at the tip 118.

Figure 39:
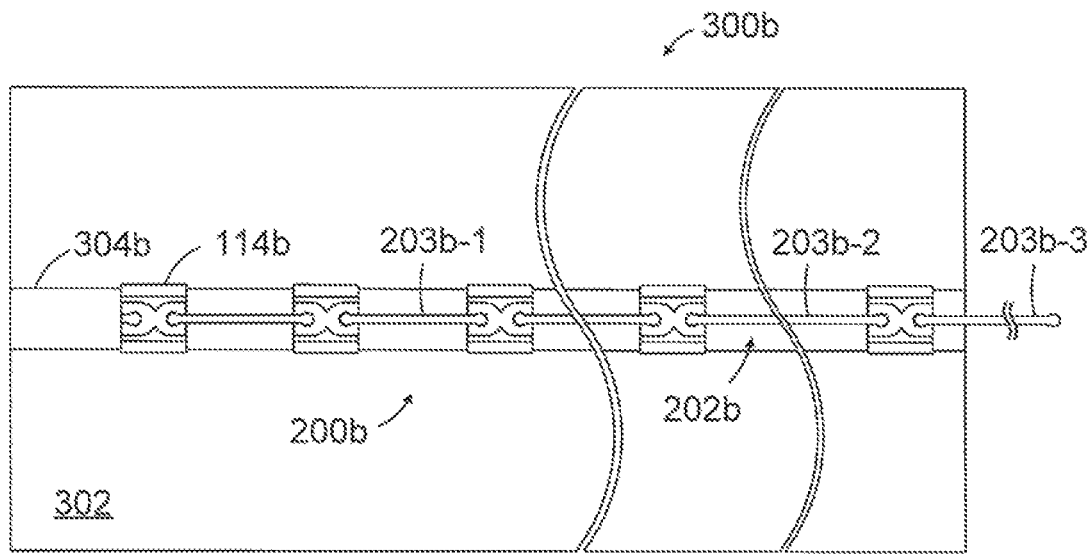
FIG. 39 is a plan view of the contact array assembly illustrated in FIG. 35 on a wire bonding fixture.

As illustrated for example in FIG. 39, the contact array assembly 200b may be positioned on a wire bonding fixture 300b, which holds the contact array assembly while the lead wires 134 are being bonded to the individual contacts 114b. The exemplary bonding fixture 300b includes a main body 302 and a channel 304b that is sized and shaped to accommodate the contacts 114b. Proper spacing of the contacts 114b is maintained by the carrier 202b and, in particular, by the links 203b. After the contact array assembly 200b has been positioned on the wire bonding fixture 300, each lead wire 134 (sixteen in the illustrated implementation) may be physically bonded and electrically connected to a respective one of the wire contact surfaces 146b in the manner illustrated in FIGS. 40 and 41. For example, the end portion of each lead wire 134 may be stripped of insulation and fed through one of the slots 156b of a contact 114b and then redirected onto the wire contact surface 146b. The end portion of each lead wire 134 may then be bonded to the wire contact surface 146b by resistance welding, wire bonding, hot bar welding, or any other suitable technique to form the bonds 134'. The bonds 134' may be created in series, starting with contact sixteen (i.e., the contact 114b that will be closest to the base 120) and ending with contact one (i.e. the contact 114b that will be closest to the tip 118), to prevent damage to the lead wires 134. In some instances, the choice of slot 156b may alternate from one contact 114b to the next and, accordingly, eight lead wires 134 will extend towards and past the reinforcement 114b' on one side of the links 203b and another eight lead wires will extend towards and past the reinforcement on the other side of the links.

The contact array assembly 200b, with wires 134 attached thereto, may thereafter be transferred to a mold into which the LSR (or other resilient material) will be injected to form the flexible body 112b. One example of such a mold is the mold 400b illustrated in FIGS. 42-44. The mold 400b is substantially similar to mold 400 and similar elements are represented by similar reference numerals. For example, the mold 400b includes first and second mold parts 402 and 404. The first mold part 402 includes a plate 406 with a contact surface 408, an elongate cavity 410, and a resilient insert 412b with a lead defining surface 416b that is configured to accommodate the contacts 114b. The second mold part 404 includes a plate 420 with a contact surface 422 and a curved lead defining surface 424b. The first and second mold parts 402 and 404 may be clamped together with the lead defining surface 416b aligned with the lead defining surface 424b, which together define a mold cavity 428b the shape of the flexible body 112b.

Figures 43, 45:
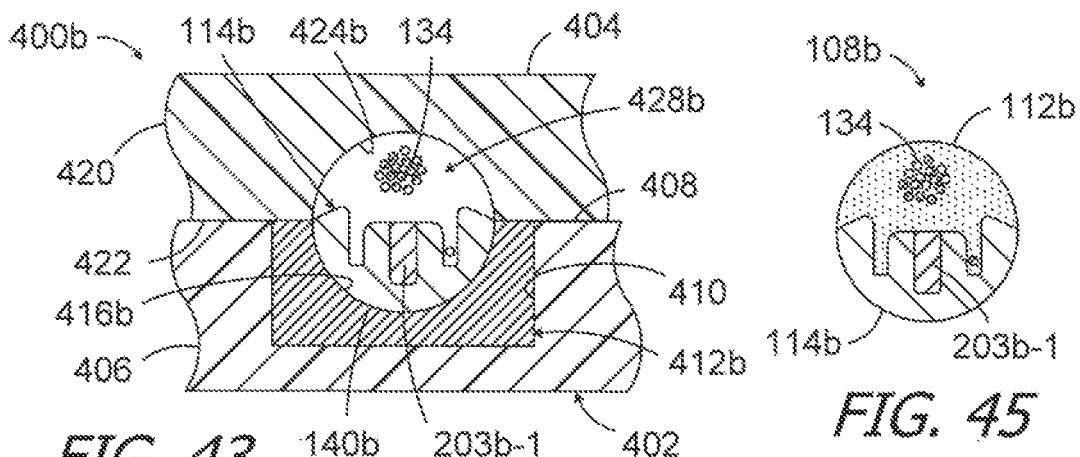
FIG. 43 is a section view taken along line 43-43 in FIG. 42.
FIG. 45 is a section view taken along line 45-45 in FIG. 31.
Figures 44, 46:
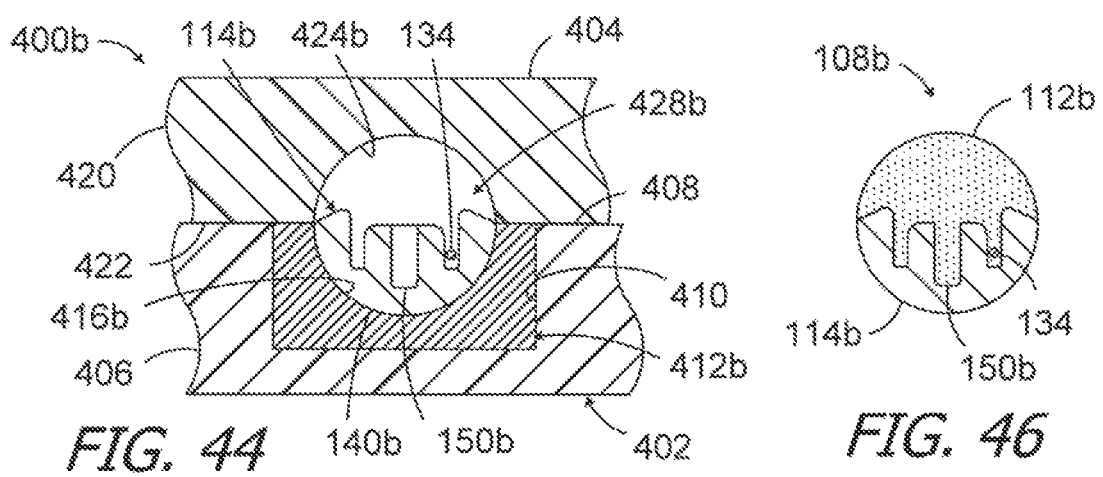
FIG. 44 is a section view taken along line 44-44 in FIG. 42.
FIG. 46 is a section view taken along line 46-46 in FIG. 31.
Figure 47:
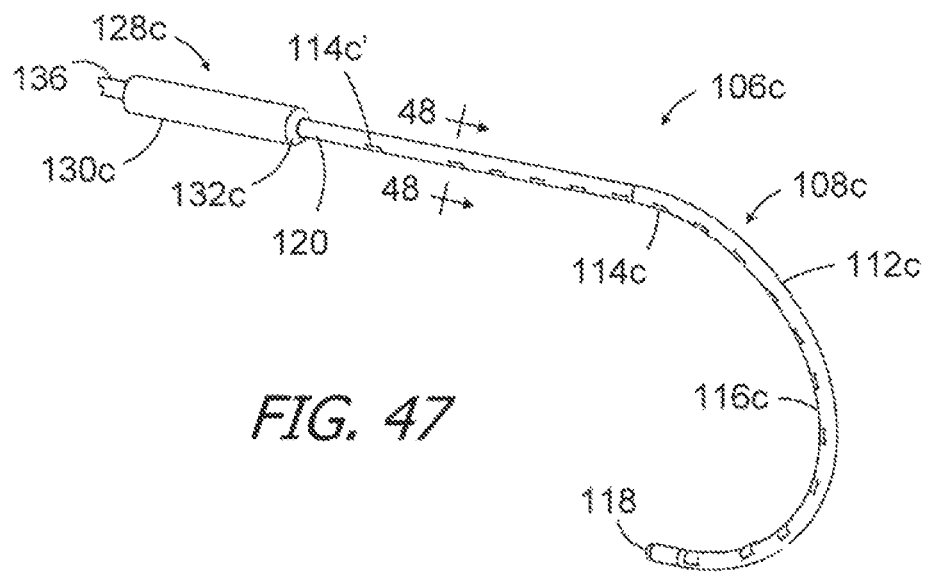
FIG. 47 is a perspective view of a portion of a cochlear lead in accordance with one embodiment of a present invention.
Figure 48:
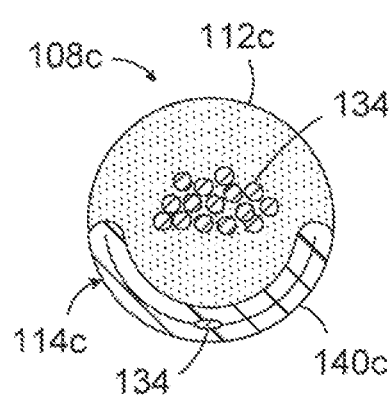
FIG. 48 is a section view taken along line 48-48 in FIG. 47.

During the molding process, the contact array assembly 200b, with wires 134 attached thereto, may be pressed into the lead defining surface 416b of the resilient insert 412b while the first and second mold parts 402 and 404 are separated, as is discussed in greater detail above in the context of mold 400. The links 203b will maintain the proper spacing between the contacts 114b, as well as between the basal-most contact 114b and the reinforcement 114b'. A portion of the carrier 202b (i.e., some of the links 203b-1)

that will not form part of the stiffener 180 may then be removed (FIG. 42) by simply moving the links in the direction of arrow B (FIG. 33), while the links that will form part of the stiffener 180 will remain attached to the associated contacts 114*b*. The lead wires 134 may then be bundled in, for example, the manner illustrated in FIG. 43. The first and second mold parts 402 and 404 may then be brought together and secured to one another, and the LSR or other suitable resilient material may then be injected (or otherwise introduced) into the mold cavity 428*b* to form the flexible body 112*b*, as shown in FIGS. 45 and 46. After the resilient material hardens, the mold parts 402 and 404 may be separated from one another. The completed electrode array 108*b* may be removed from the insert 412*b* by, for example, simply pulling the completed flexible body 112*b* out of the insert.

There are some instances where it may be desirable to pre-curve the cochlear lead. One example of a cochlear lead that includes a pre-set curvature is the cochlear lead 106*c* illustrated in FIG. 47. The cochlear lead 106*c* is substantially similar to the cochlear lead 106 described above with reference to FIGS. 1-18. For example, the cochlear lead 106*c* includes an electrode array 108*c* with a curved flexible body 112*c* and a plurality of electrically conductive contacts 114*c* (e.g., sixteen contacts) between the tip 118 and the base 120 that are connected to lead wires 134. A wing 128*c*, with a cylindrical portion 130*c* and a tapered portion 132*c*, is located at the electrode array base 120. A marker contact 114*c'*, which is not connected to a lead wire, is located adjacent to the base 120. The cochlear lead 106*c* may also be incorporated into the cochlear implant 100 in place of the lead 106.

Figure 49:
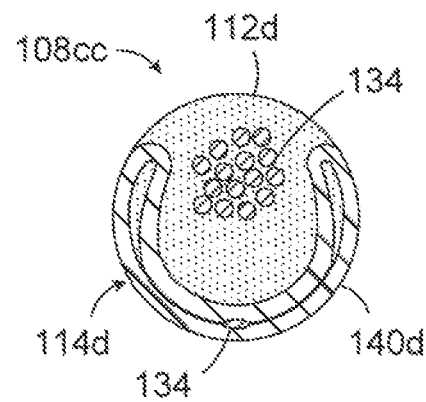
FIG. 49 is a section view of a portion of a cochlear lead in accordance with one embodiment of a present invention.
Figure 50:
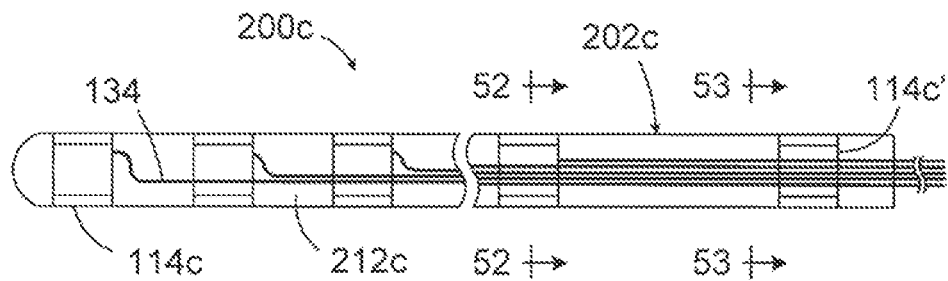
FIG. 50 is a plan view of a contact array assembly in accordance with one embodiment of the present invention.
Figure 51:
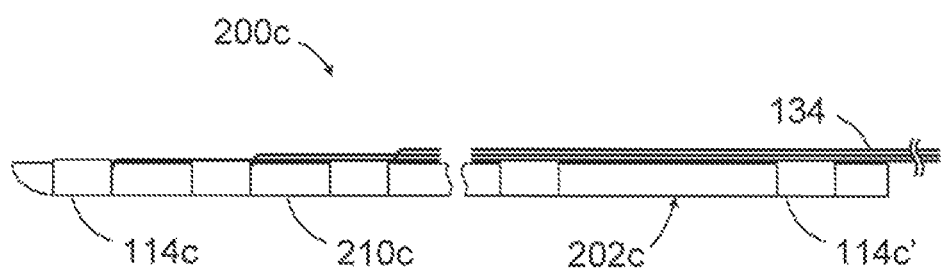
FIG. 51 is a side view of the contact array assembly illustrated in FIG. 50.
Figure 52:
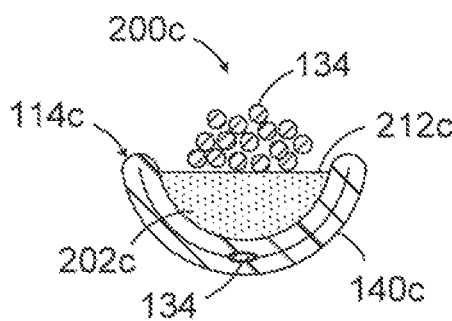
FIG. 52 is a section view taken along line 52-52 in FIG. 50.
Figure 53:
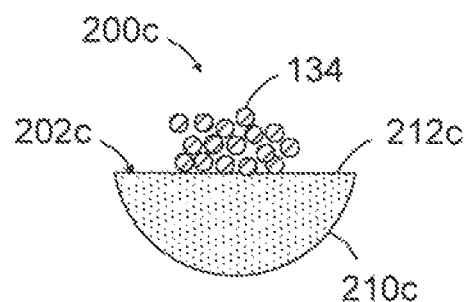
FIG. 53 is a section view taken along line 53-53 in FIG. 50.

The exemplary electrode array 108*c* has a circular cross-section and the curved tissue contact surfaces 140*c* of the contacts 114*c* extend about one-half of the way around (i.e., about 180 degrees around) the perimeter of the array. The contacts may, however, have tissue contact surfaces that extend more or less than one-half of the way around the perimeter in other implementations. For example, the electrode array 108*cc* illustrated in FIG. 49 is otherwise identical to electrode array 108*c* and includes a plurality of contacts 114*d* on a curved flexible body 112*d*. The contacts 114*d* have curved tissue contact surfaces 140*d* that extend more than one-half of the way around (i.e., more than 180 degrees around) the perimeter of the cross-section.

Contacts such as contacts 114*c* and marker 114*c'* may form part of a contact array assembly that is used during the formation of the exemplary electrode array 108*c*. The contacts 114*c* and marker 114*c'* in the exemplary contact array assembly 200*c* illustrated in FIGS. 50-53 are positioned on a carrier 202*c*. The contact array assembly 200*c* also includes the lead wires 134. The carrier 202*c* may be formed from the same material as, and ultimately becomes part of, the flexible body 112*c*. To that end, the carrier 202*c* includes a curved bottom surface 210*c*, which will become part of the curved bottom surface 116*c* of the flexible body 112*c*, and a top surface 212*c*. The lead wires 134 are secured to the remainder of the contact array assembly 200*c* in such a manner that the lead wires are less likely to break, as compared to conventional assemblies, when the contact array assembly 200*c* is inserted into a curved mold. In particular, each of the lead wires 134 may be secured only to the associated contact 114*c* and positioned on top of the carrier top surface 212*c* (as opposed to molding the lead wires into the carrier 202*c*). As a result, when the straight contact array assembly 200*c* is pressed into a curved mold in, for example, the manner described below with reference to FIGS. 70-72, the lead wires 134 will be free to move relative to the carrier 202*c* and will be less likely to break due to tension.

Figure 54:
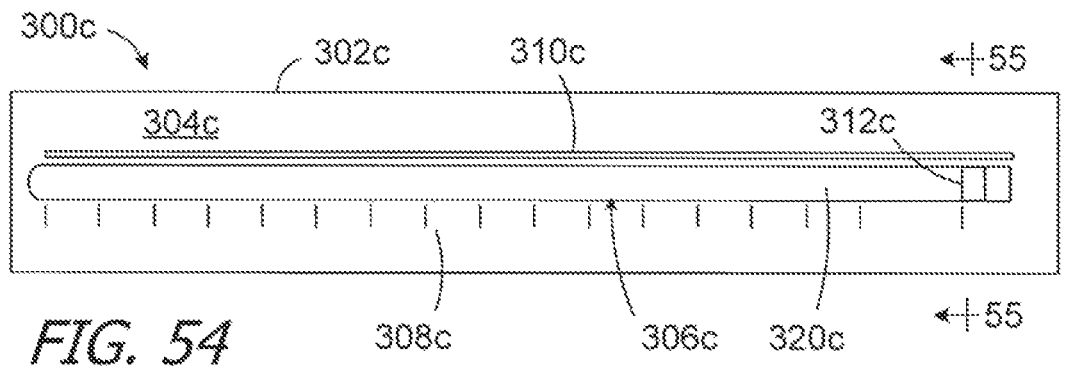
FIG. 54 is a plan view of a portion of an exemplary method of manufacturing the contact array assembly illustrated in FIG. 50 in accordance with one embodiment of a present invention.

The exemplary contact array assembly 200*c* may be formed in the exemplary fixture 300*c* illustrated in FIG. 54 in accordance with the method described below with reference to FIGS. 55-62. The fixture 300*c* includes a plate 302*c* with a top surface 304*c* and an elongate cavity 306*c* with a curvature corresponding to that of the electrode array 108*c*. The top surface 304*c* includes markers 308*c* which correspond to the intended locations of the contacts 114*c*. Here, there is a single marker 308*c* for each of the contacts 114*c*. In another implementation (not shown), a set of four markers 308*c* (two on each side of the cavity 306*c*) may be provided for each of the contacts 114*c*. A wire rest 310*c* extends upwardly from the top surface 304*c*.

Figure 55:
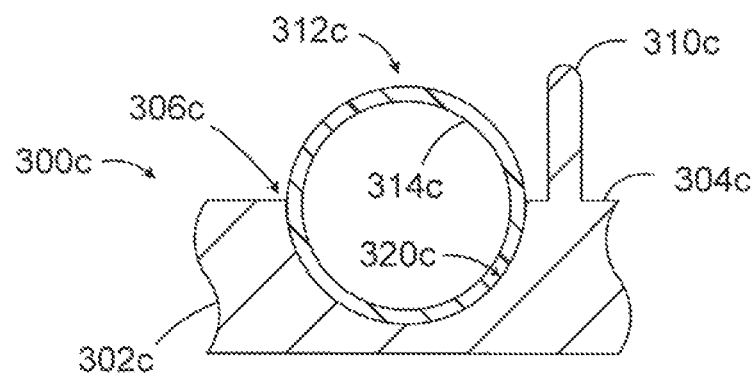
FIG. 55 is a section view of a portion of the exemplary method of manufacturing the contact array assembly illustrated in FIG. 50.
Figure 56:
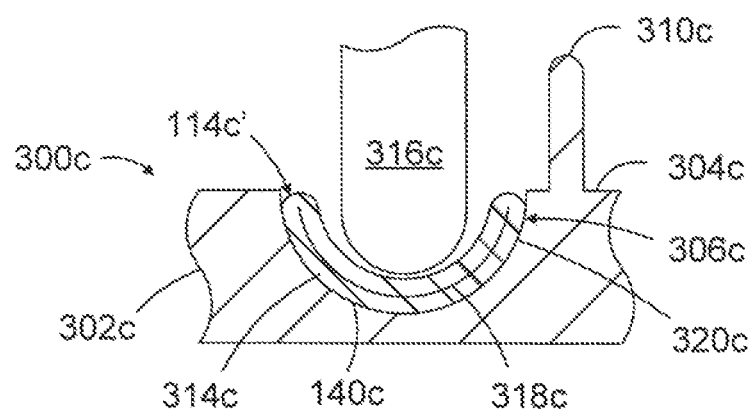
FIG. 56 is a partial section view of a portion of the exemplary method of manufacturing the contact array assembly illustrated in FIG. 50.

The fixture 300*c* may in some instances be a disposable part formed by a photoetching process. Although iron and other photoetchable materials may be employed, the fixture 300*c* is formed from copper, which is relatively inexpensive and has a number of advantageous properties. Copper is unlikely to bond to platinum contacts 114*c* because copper does not weld easily and has relatively high thermal conductivity, which causes heat to dissipate very readily. Copper is also resilient in that it will flex slightly and return to its shape when the platinum contact workpieces (discussed below) are pressed through the opening. Copper is easy to bend, which facilitates release of the electrode array (discussed below). Also, as copper is electrically conductive, it may be used in an opposed weld process where the copper fixture 300*c* forms part of the electrical loop. In other implementations, the fixture 300*c* may be a reusable apparatus that consists of two separable pieces formed from a harder material such as stainless steel The exemplary method involves placing contact workpieces 312*c* into the cavity 306*c* at locations corresponding to the contacts 114*c* and marker 114*c'*, as well as placing one end of a lead wire 134 into each workpiece in the case of the contacts 114*c*, and then applying heat and pressure to the workpiece. Referring first to FIGS. 54 and 55, the exemplary contact workpiece 312*c* is a tube defined by a wall 314*c* formed from platinum or other suitable contact material. Although not limited to any particular shape, the exemplary workpiece is a cylindrical tube and is circular in cross-section. The workpiece 312*c* illustrated in FIGS. 54 and 55 will form the marker 114*c'* The heat and pressure causes compression and distortion of the malleable workpiece 312*c* as shown in FIG. 56. Portions of the wall 314*c* will come into contact with one another along a seam 318*c*. In some instances, gaps (not shown) may remain between some portions of the wall. The gaps augment the mechanical interconnection between the carrier 202*c* and the contacts 114*c*.

The heat and pressure may be applied with, for example, a weld tip, such as the molybdenum weld tip 316*c*, in a resistance welding process. In other implementations, the marker 114*c'* and contacts 114 may be formed by compressing the workpiece 312*c* with a stainless steel weld tip (no heat applied) and then applying heat with a molybdenum weld tip, thereby preventing wear on both weld tips.

Figure 57:
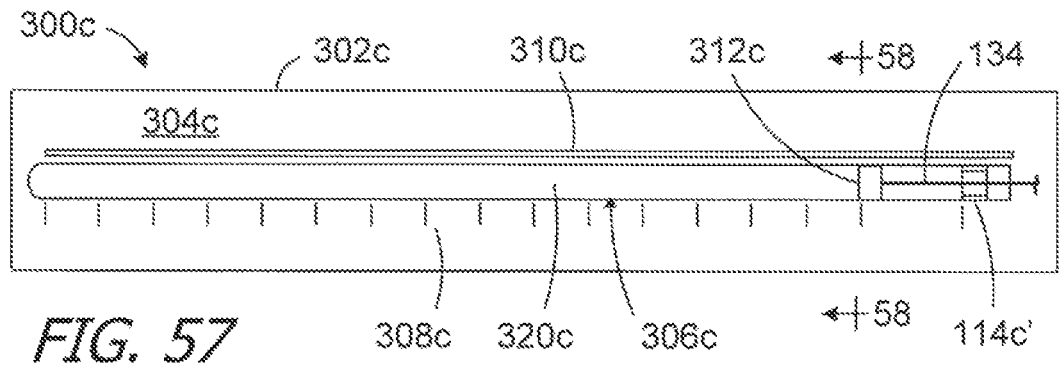
FIG. 57 is a plan view of a portion of the exemplary method of manufacturing the contact array assembly illustrated in FIG. 50.
Figure 58:
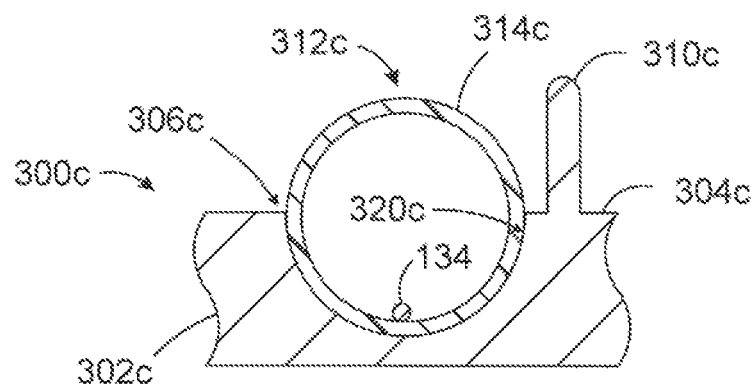
FIG. 58 is a section view of a portion of the exemplary method of manufacturing the contact array assembly illustrated in FIG. 50.
Figure 59:
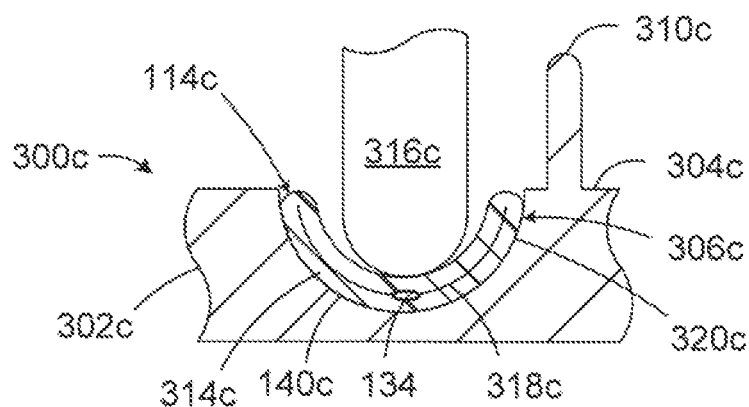
FIG. 59 is a partial section view of a portion of the exemplary method of manufacturing the contact array assembly illustrated in FIG. 50.

Turning to FIGS. 57 and 58, formation of the contact 114*c* closest to the marker 114*c'* (as well as the other contacts) involves placing a workpiece 312*c* into the cavity 306*c* and placing the end of the lead wire 134 into the workpiece. Heat and pressure may then be applied to the workpiece 312*c* to form the contact 114*c*, and bond the end of the lead wire 134 to the contact, in the manner illustrated in FIG. 59. It should also be noted that the marker 114c' and contact 114 are pressed tightly against the mold surface 320c that defines the cavity 306c, thereby preventing movement of the marker and contact and also masking the curved tissue contact surfaces 140c of the marker and contact. The mold surface 320c also defines a portion of the outer surface of carrier 202c in the spaces not covered by the contacts 114c.

Figure 60:
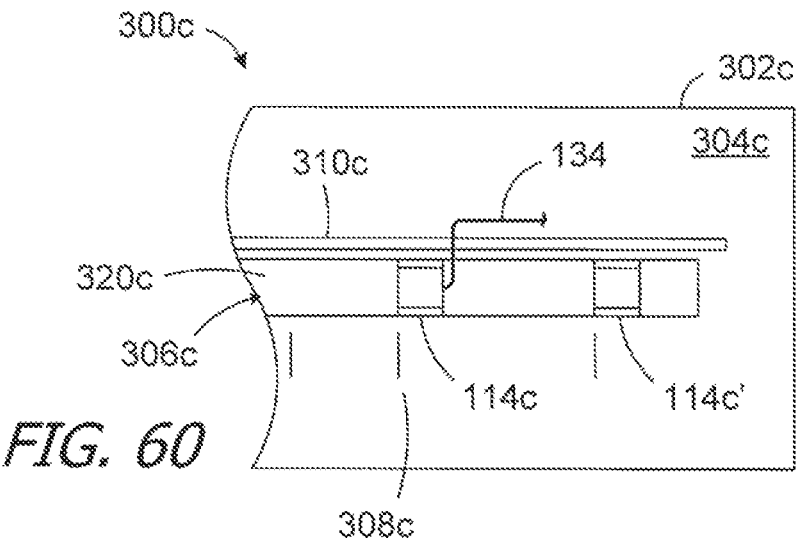
FIG. 60 is a plan view of a portion of the exemplary method of manufacturing the contact array assembly illustrated in FIG. 50.
Figure 61:
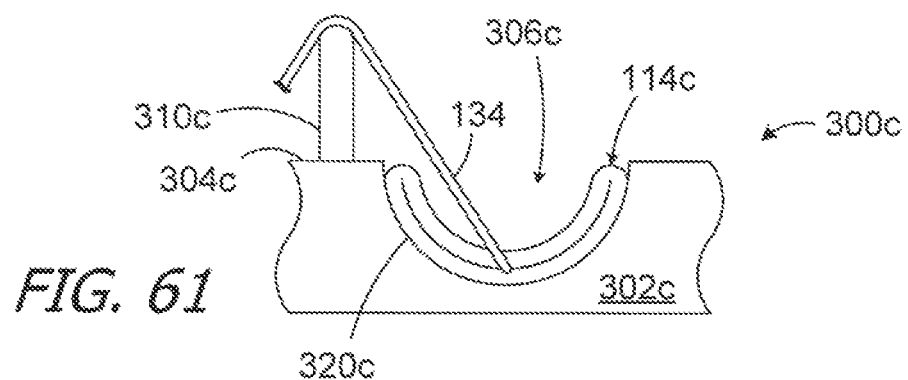
FIG. 61 is an end view of a portion of the exemplary method of manufacturing the contact array assembly illustrated in FIG. 50.

Turning to FIGS. 60 and 61, one end of the associated lead wire 134 will be secured to the associated contact 114c, and therefore immovable relative to the contact, after the contact is formed. The remainder of the lead wire 134 may be moved out of the cavity 306c. As a result, the portion of the lead wire 134 that is coextensive with the carrier 202c will not be molded into carrier. In the illustrated implementation, the lead wire 134 may be directed over the wire rest 310c.

Figure 62:
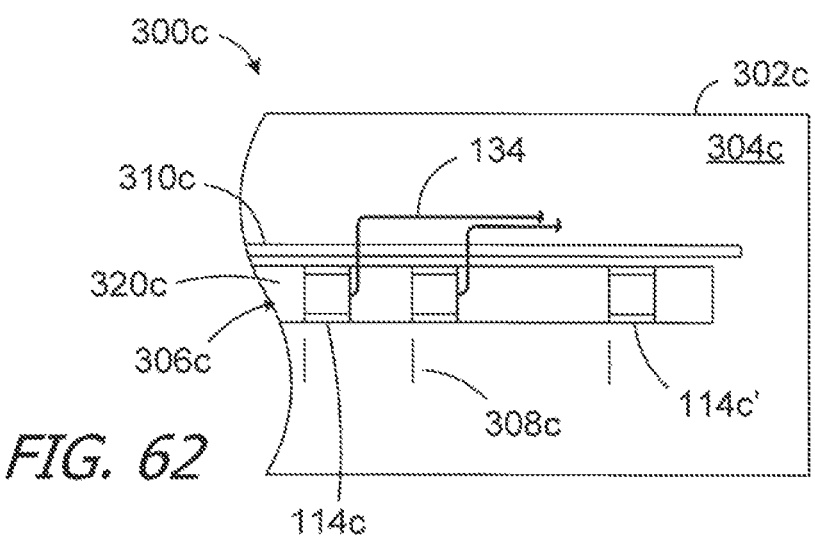
FIG. 62 is a plan view of a portion of the exemplary method of manufacturing the contact array assembly illustrated in FIG. 50.
Figure 63:
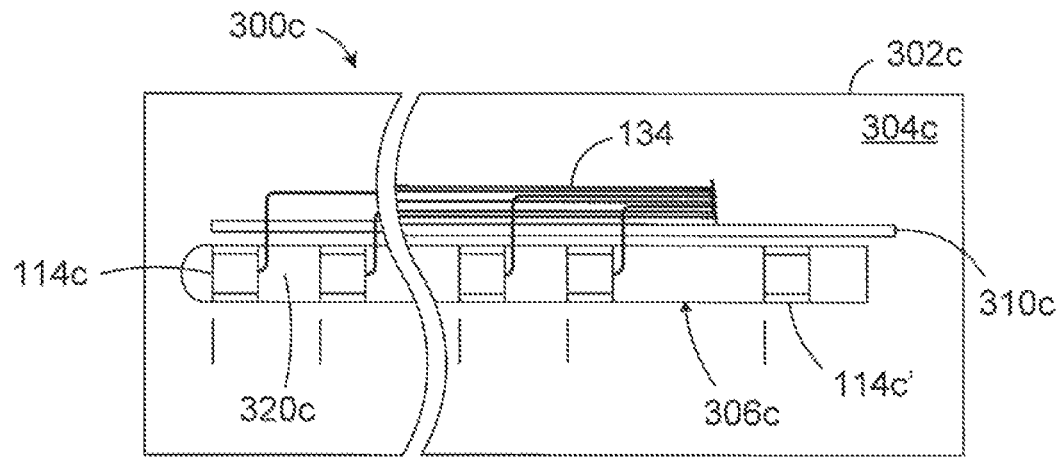
FIG. 63 is a plan view of a portion of the exemplary method of manufacturing the contact array assembly illustrated in FIG. 50.

The steps described above with reference to FIGS. 57-61 may then be repeated to form the remainder to the contacts 114c. Referring to FIGS. 62 and 63, after each contact 114c is formed by compressing workpiece 312c onto the end of the associated lead wire 134, the lead wires may be may be directed out of the cavity and over the wire rest 310c.

Figure 64:
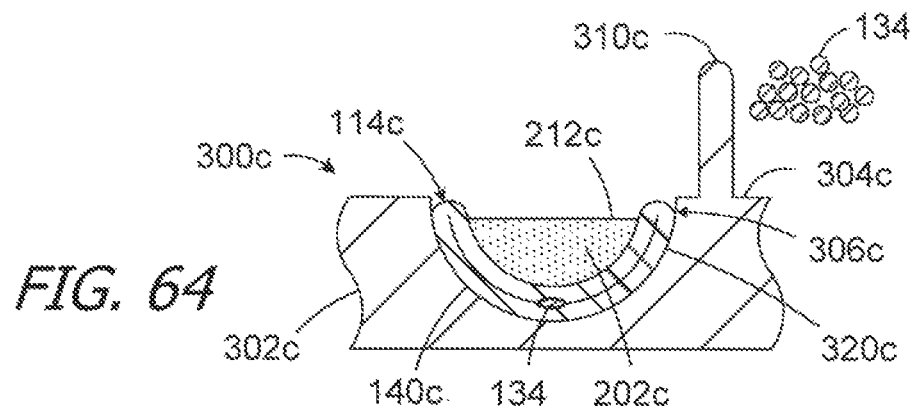
FIG. 64 is a section view of a portion of the exemplary method of manufacturing the contact array assembly illustrated in FIG. 50.
Figure 65:
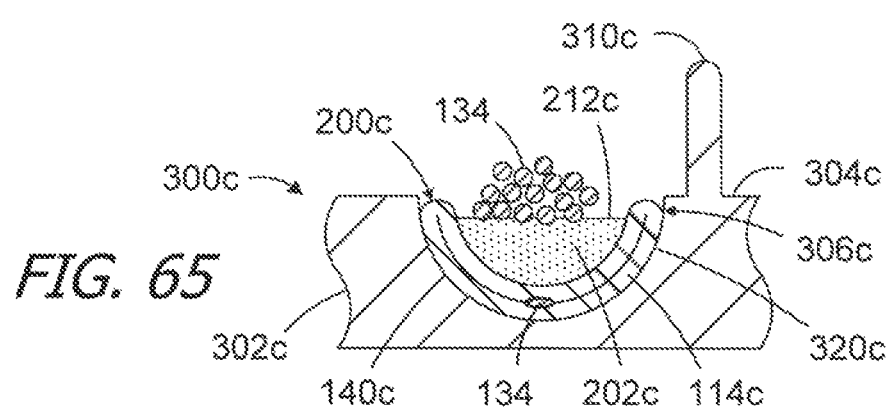
FIG. 65 is a section view of a portion of the exemplary method of manufacturing the contact array assembly illustrated in FIG. 50.
Figure 66:
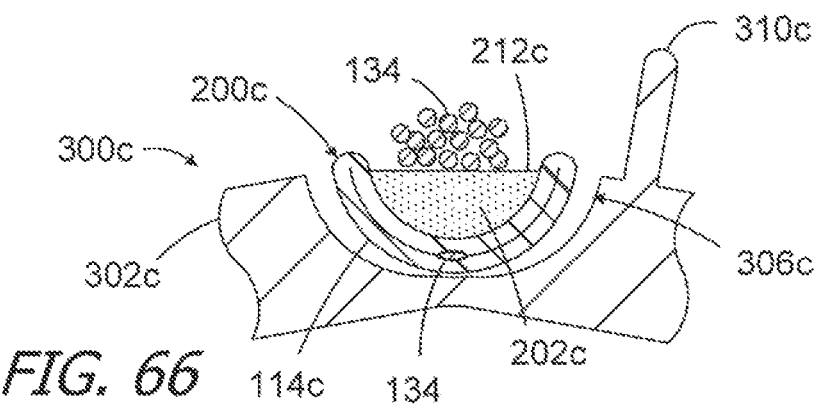
FIG. 66 is a section view of a portion of the exemplary method of manufacturing the contact array assembly illustrated in FIG. 50.
Figure 67:
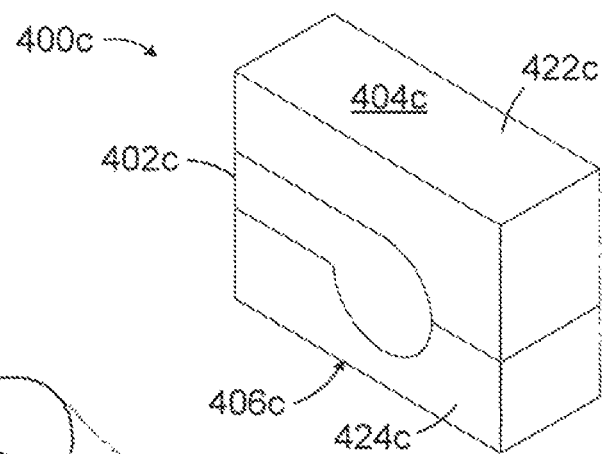
FIG. 67 is a perspective view of a mold in accordance with one embodiment of a present invention.
Figure 68:
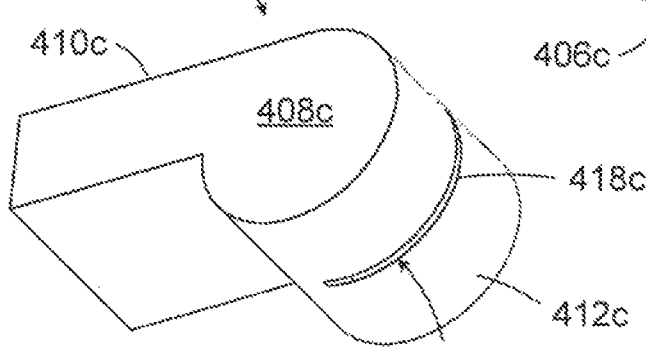
FIG. 68 is a perspective view of a portion of the mold illustrated in FIG. 67.
Figure 69:
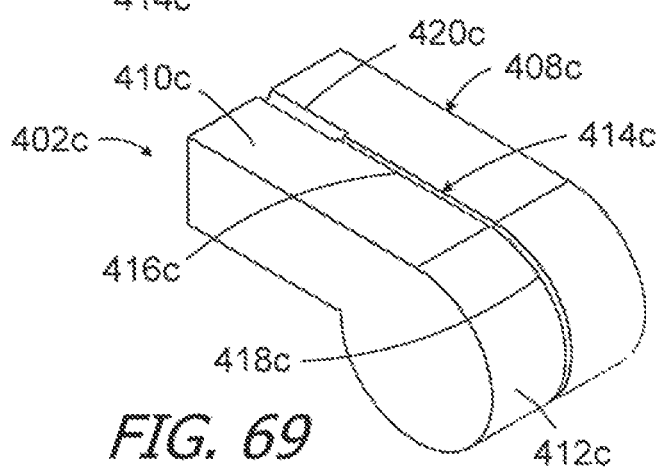
FIG. 69 is a perspective view of a portion of the mold illustrated in FIG. 67.
Figure 70:
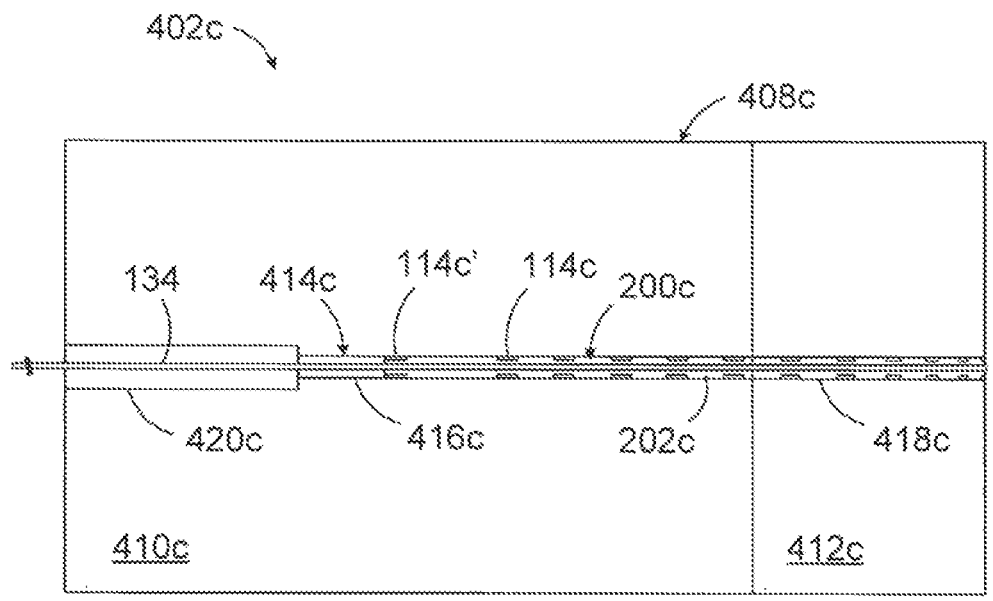
FIG. 70 is a plan view of the contact array assembly illustrated in FIG. 50 on a portion of the mold illustrated in FIG. 67.
Figure 71:
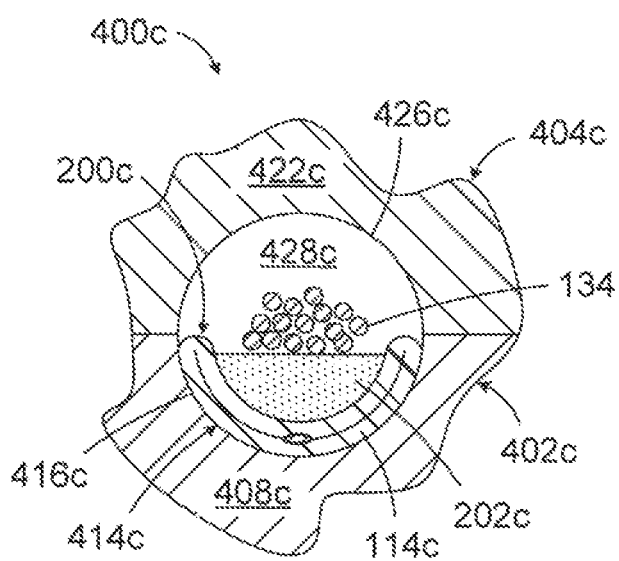
FIG. 71 is a section view of the contact array assembly illustrated in FIG. 50 within the mold illustrated in FIG. 67.
Figure 72:
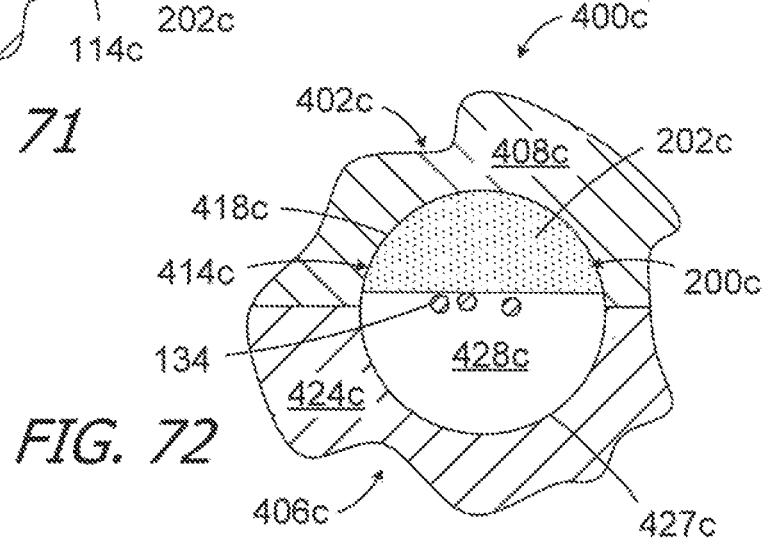
FIG. 72 is a section view of the contact array assembly illustrated in FIG. 50 within the mold illustrated in FIG. 67.
Figure 73:
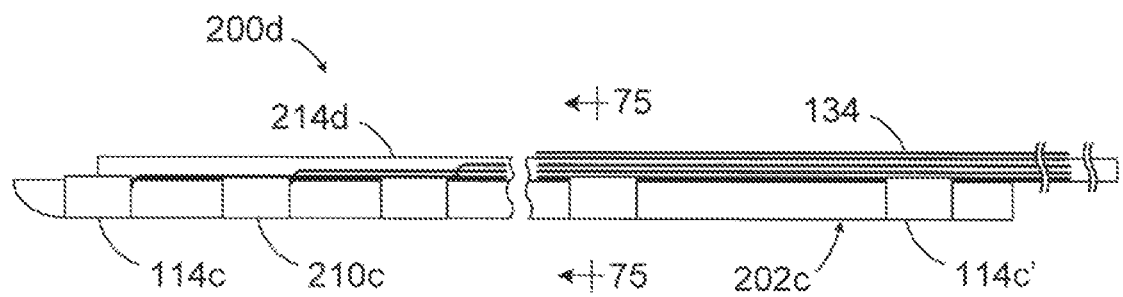
FIG. 73 is a side view of a contact array assembly in accordance with one embodiment of the present invention.

Once all of the contacts 114c have been formed, and while the lead wires 134 remain outside of the cavity 306c, LSR or other suitable resilient material may then be injected (or otherwise introduced) into the cavity 306c as shown in FIG. 64 to form the carrier 202c. After the resilient material has cured to such an extent that the lead wires 134 will not sink into it, the lead wires may be positioned on the top surface 212c (FIG. 65) to complete the contact array assembly 200c. The contact array assembly 200c may be removed from the fixture 300c by simply pulling the assembly out of the cavity 306c. Referring to FIG. 66, bending of the plate 302c may be required in some instances when removing the contact array assembly 200c from the cavity 306c.

The contact array assembly 200c may then be placed into a mold to form the remainder of the curved cochlear lead 106c. Referring to FIGS. 67-70, one example of such a mold is the mold 400c with mold parts 402c-406c. The mold part 402c includes a block 408c with straight and curved portions 410c and 412c. A semi-circular lead defining surface 414c, with straight and curved portions 416c and 418c, is formed in the straight and curved portions 410c and 412c of the block 408c. A semi-circular surface 420c with a shape corresponding to a portion of the wing 128c is also formed in the straight portion 410c. In some instances, a resilient insert (not shown) similar to the insert 412 described above with reference to FIGS. 22-27 may be provided. The mold parts 404c and 406c respectively include blocks 422c and 424c with semi-circular lead defining surfaces 426c and 427c (FIGS. 71 and 72) which, together with the lead defining surface 414c, define the mold cavity 428c (FIGS. 71 and 72) that is used to form the flexible body 112c. The mold part 404c also includes a semi-circular surface (not shown) with a shape corresponding to a portion of the wing 128c.

After insertion of the contact array assembly 200c, and prior to injection of the LSR (or other resilient material), the mold parts 402c-406c may be clamped together with the lead defining surfaces 414c, 426c and 427c aligned in the manner described above to define a mold cavity 428c the shape of the flexible body 112c. The LSR or other suitable resilient material may then be injected (or otherwise introduced) into the mold cavity 428c to form the flexible body 112c. After the resilient material hardens, the mold parts 402c-406c may be separated from one another and the completed electrode array 108c may be removed.

Some cochlear leads with pre-set curvatures are straightened prior to the insertion process by a stylet or other stiffening element that is inserted into a stylet lumen within the electrode array. The present contact array assemblies may be configured to provide such a stylet lumen. To that end, and referring for example to FIG. 73, the exemplary contact array assembly 200d is substantially similar to contact array assembly 200c and similar elements are identified by similar reference numerals. For example, the contact array assembly 200d includes the contacts 114c and marker 114c', carrier 202c (with bottom and top surfaces 210c and 212c), and the lead wires 134. Here, however, the contact array assembly 200d also includes a hollow tube 214d. The tube 214d may be added to the remainder of the contact array assembly 200d either before or after the contact array assembly is placed into a mold (e.g., mold 400c in FIG. 67). Suitable materials for the tube 214d include, but are not limited to, silicone elastomers such as Silastic® silicone elastomer from Dow Corning.

Figure 74:
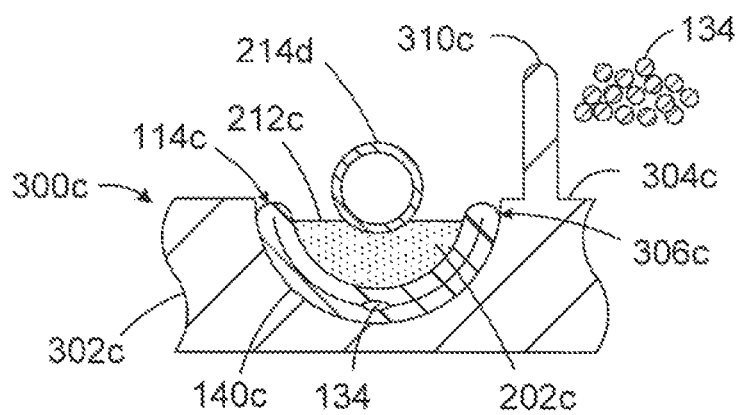
FIG. 74 is a section view of a portion of an exemplary method of manufacturing the contact array assembly illustrated in FIG. 73 in accordance with one embodiment of a present invention.
Figure 75:
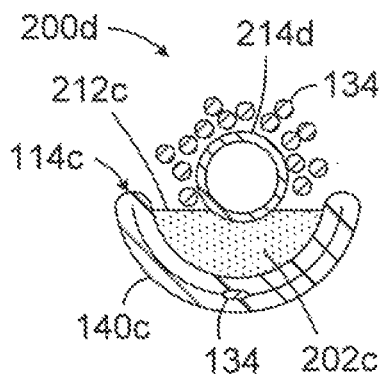
FIG. 75 is a section view taken along line 75-75 in FIG. 73.
Figure 75A:
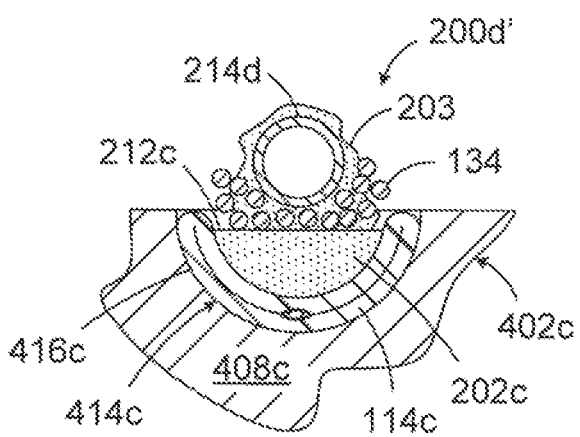
FIG. 75A is a section view of a portion of an exemplary method of manufacturing a contact array assembly in accordance with one embodiment of a present invention.

Referring to FIG. 74, in those instances where the tube 214d is added to the remainder of the contact array assembly 200d prior to placement into the mold, the tube may be positioned on (and pressed slightly into) the LSR or other resilient material which forms the carrier 202c prior to the material hardening and prior to the lead wires 134 be positioned over the top surface 212c. The lead wires 134 may then be positioned on and over the tube 214d and the carrier 202c, as is shown in FIG. 75. Turning to FIG. 75A, in those instances where the tube 214d is added after the other portions of the contact array assembly have been placed onto a portion of curved mold (such as the mold part 402c), the tube may be bent around the carrier 202c and placed over the lead wires 134. Small spaced quantities 203 of the LSR or other resilient material that forms the carrier 202c may be applied to hold the tube 214c in place and complete the contact array assembly 200d'. The molding process may then proceed in the manner described above.

Figure 76:
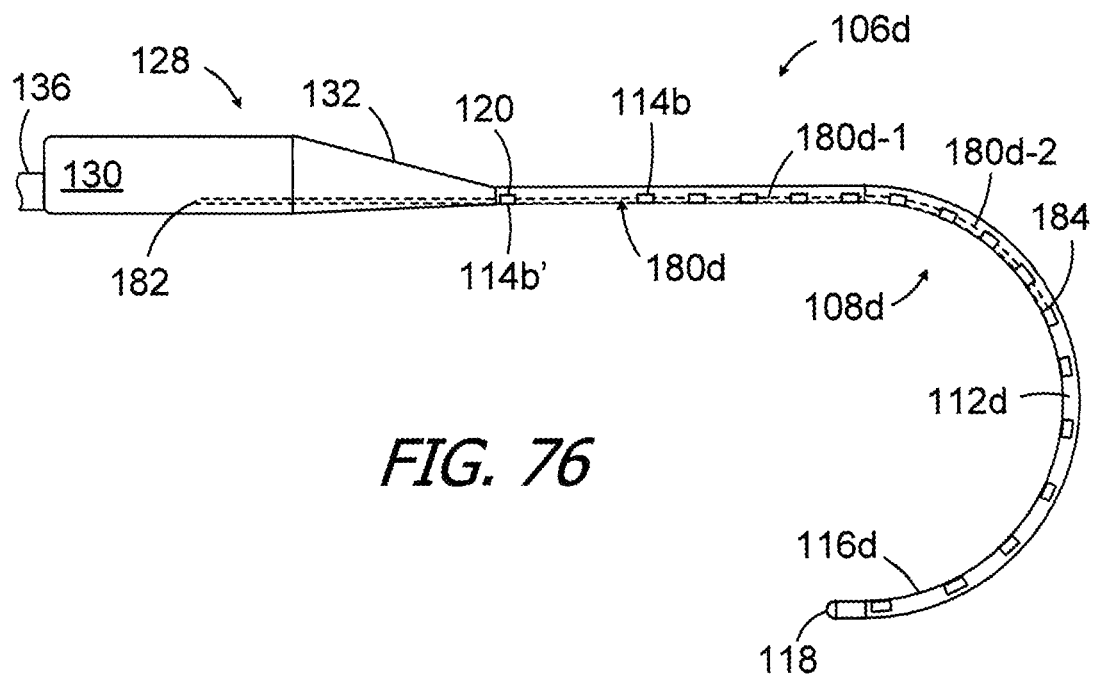
FIG. 76 is a side view of a portion of cochlear lead in accordance with one embodiment of a present invention.
Figure 77:
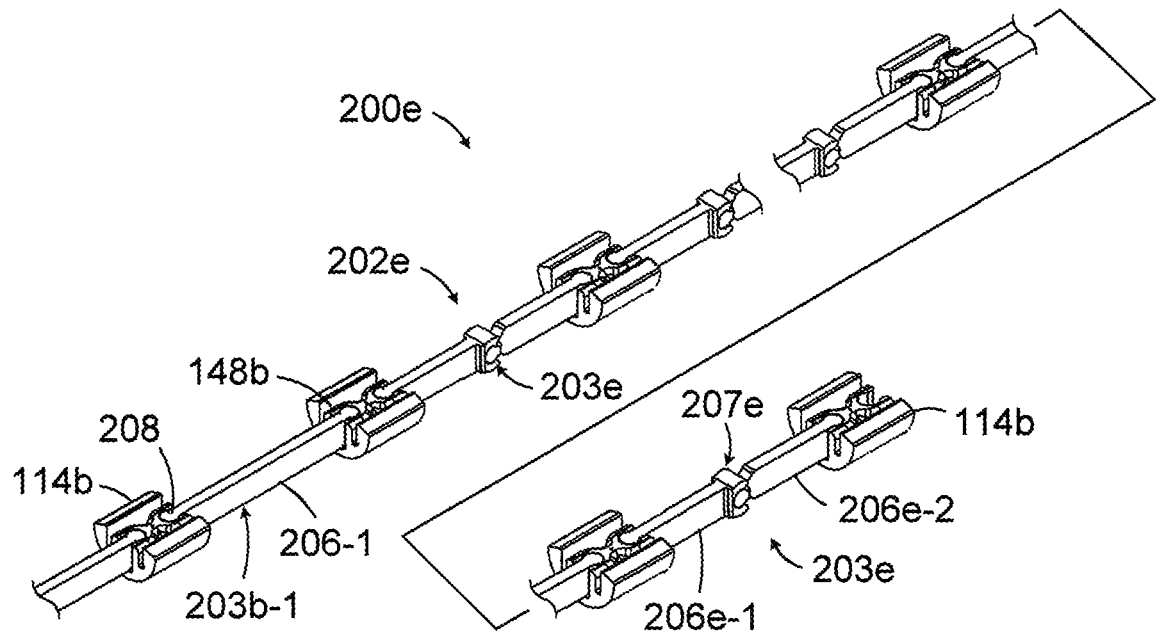
FIG. 77 is a perspective view of a contact array assembly in accordance with one embodiment of the present invention.

There are some instances where it may be desirable to pre-curve a cochlear lead that includes a stiffener. One example of a cochlear lead that includes a pre-set curvature and a stiffener is the cochlear lead 106d illustrated in FIG. 76. The cochlear lead 106d includes various aspects of the above-described cochlear leads 106b and 106c and similar elements are represented by similar reference numerals. For example, the cochlear lead 106d includes an electrode array 108d with a curved flexible body 112d and a plurality of electrically conductive contacts 114b (e.g., sixteen contacts) on the curved bottom surface 116d between the tip 118 and the base 120. The contacts 114b are connected to lead wires in the manner described above. A wing 128, with a rectangular portion 130 and a tapered portion 132, is located at the electrode array base 120. The end portion of the base 120 may include a reinforcement 114b' which, as noted above, is a contact 114b that is not connected to a lead wire. The cochlear lead 106d may also be incorporated into the cochlear implant 100 in place of the lead 106.

The exemplary cochlear lead 106d also includes a stiffener 180d having first and second stiffener portions 180d-1 and 180d-2. The first stiffener portion 180d-1 may be associated with the four active contacts 114b closest to the base 120 (i.e., contacts thirteen to sixteen) as well as the reinforcement 114b', and may also extend into the wing 128. The second stiffener portion 180d-2 may be associated with a common contact 114b that is also associated with the first stiffener portion 180d-1 as well as an additional six contacts (i.e., contacts thirteen to seven). The first stiffener portion 180d-1 may be identical to the stiffener 180 described above with reference to FIGS. 31-46, while the second stiffener portion 180d-2 is configured to both provide axial stiffness and to accommodate the curvature of the curved portion of the flexible body 112d, bending of the electrode array 108d that occurs during insertion into the cochlea, and placement of the associated contact array assembly into a curved mold in a manner similar to the mold described above with reference to FIGS. 67-70.

The exemplary stiffener 180d, which has ends 182 and 184, may be formed from portions of a contact array assembly that is used in the manufacturing process. Referring to FIGS. 77-80, the exemplary contact array assembly 200e is substantially similar to contact array assembly 200b (FIGS. 32-41) and similar elements are represented by similar reference numerals. For example, the exemplary contact array assembly 200e includes the aforementioned plurality of electrically conductive contacts 114b as well as a carrier 202e that includes plurality of relatively stiff, electrically non-conductive links. In particular, the carrier 202e includes a link 203b-1 and a link 203b-2 (see FIG. 32) as well as a plurality of links 203b-3, all of which are described above. There are three links 203b-3, which connect contacts thirteen through sixteen, in the illustrated sixteen contact implementation. The carrier 202e also includes a plurality of jointed links 203e. The jointed links 203e form the remainder of the links in the contact array assembly 200e, and connect contacts one through thirteen. Each jointed link 203e is configured to allow at least one portion of the link to pivot relative to another portion, As is discussed in greater detail below, the links 203b-1 to 203b-3 will form the first stiffener portion 180d-1, while at least some of the jointed links 203e will form the second stiffener portion 180d-2. Other jointed links 203e may be removed prior to the formation of the flexible body.

Figure 78:
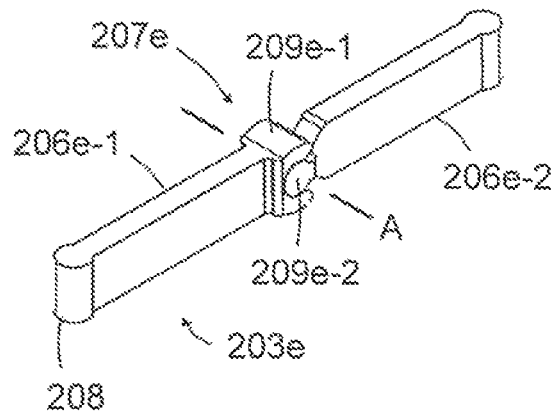
FIG. 78 is a perspective view of a portion of the contact array assembly illustrated in FIG. 77.
Figure 79:
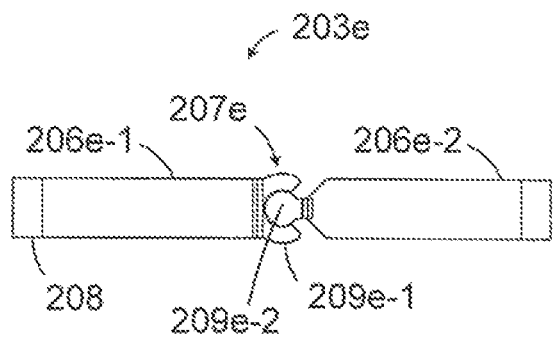
FIG. 79 is a side view of a portion of the contact array assembly illustrated in FIG. 77.
Figure 80:
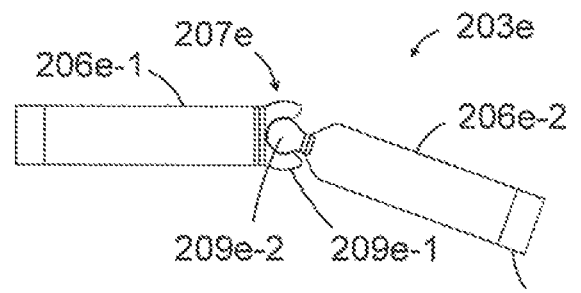
FIG. 80 is a side view of a portion of the contact array assembly illustrated in FIG. 77.

The exemplary links 203e, which may be formed from the same material as the links 203b, each include first and second rods 206e-1 and 206e-2 that are connected to one another by a joint 207e, One end of each of the rods 206e-1 and 206e-2 includes a connector 208. The connectors 208 are configured to engage with, and disengage from, corresponding connectors 148b on the contacts 114b in the manner described above. The other ends of the rods 206e-1 and 206e-2 respectively include joint members 209e-1 and 209e-2 (FIGS. 78-80). Although the present joints are not limited to any particular configuration, the joint members 209e-1 and 209e-2 in the illustrated embodiment are C-shaped and cylindrical, respectively, and allow the first and second rods 206e-1 and 206e-2 to pivot relative to one another about an axis A from, for example, the rod positions illustrated in FIGS. 78-79 to, for example, the rod positions illustrated in FIG. 80.

With respect to the formation of the cochlear lead 106d, the contact array assembly 200e may be placed into a wire bonding fixture, such as the wire boding fixture 300b (FIG. 39), and the lead wires may then be bonded to the individual contacts 114b in the manner described above with reference to FIGS. 39-41. The contact array assembly 200e, with lead wires attached thereto, may thereafter be transferred onto the appropriate mold part of a curved mold. The curved mold may be similar to the mold 400c (FIGS. 67-70). The links 203b-1 to 203b-3 will be on the straight portion of the mold, while the jointed links 203e will be on the curved portion of the mold and, in at least some instances, also on the straight portion. The links 203b-1 to 203b-3 will remain in place to form the first stiffener portion 108d-1, Some of the jointed links 203e may be removed (e.g., the jointed links between contacts one to seven) prior to the closing the mold, and the remaining jointed links will form the second stiffener portion 108d-2. After the mold parts have been damped together in the manner described above to define a mold cavity in the shape of the flexible body 112d, the LSF or other suitable resilient material may be injected (or otherwise introduced) into the mold cavity to form the flexible body. After the resilient material hardens, the mold parts may be separated from one another and the completed electrode array 108d may be removed.

Figure 81:
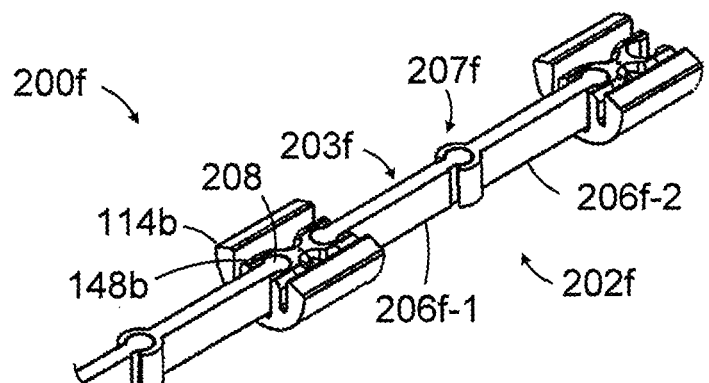
FIG. 81 is a perspective view of a portion of a contact array assembly in accordance with one embodiment of the present invention.
Figure 82:
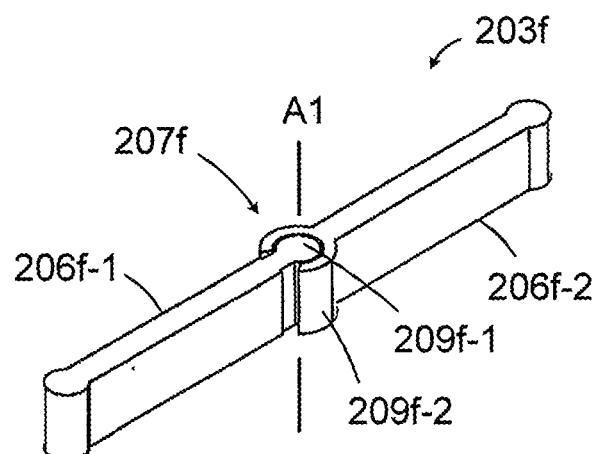
FIG. 82 is a perspective view of a portion of the contact array assembly illustrated in FIG. 81.
Figure 83:
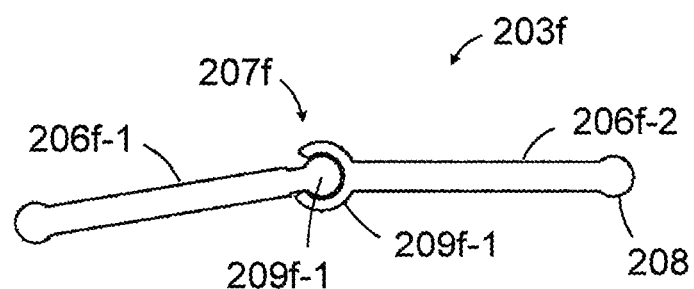
FIG. 83 is a top view of a portion of the contact array assembly illustrated in FIG. 81.
Figure 84:
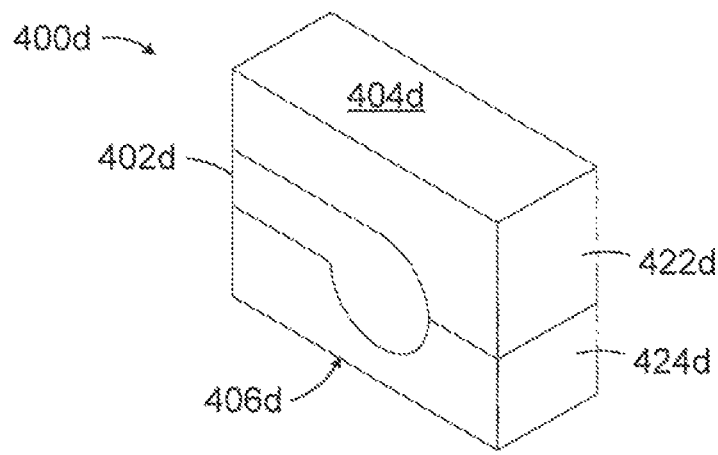
FIG. 84 is a perspective view of a mold in accordance with one embodiment of a present invention.

In other implementations, contact array assemblies may be provided with jointed links that pivot in other directions. By way of example, but not limitation, the exemplary contact array assembly 200f illustrated in FIG. 81 is identical to the contact array assembly 200e but for the use of jointed links 203f in the carrier 202f in place of jointed links 203e. Here too, the exemplary links 203f each include first and second rods 206f-1 and 206f-2 that are connected to one another by a joint 207f. One end of each of the rods 206f-1 and 206f-2 includes a connector 208. The other ends of the rods 206f-1 and 206f-2 respectively include joint members 209f-1 and 209f-2. Although the present joints are not limited to any particular configuration, the joint members 209f-1 and 209f-2 in the illustrated embodiment are cylindrical and C-shaped, respectively, and allow the first and second rods 206f-1 and 206e-2 to pivot relative to one another about an axis A1 from, for example, the rod positions illustrated in FIGS. 81-82 to, for example, the rod positions illustrated in FIG. 83. The axis A1 is offset from axis A (FIG. 78) by 90 degrees. One exemplary use of the contact array assembly 200f is the formation of an electrode array of the type described below with reference to FIG. 84.

In still other implementations, the jointed links may be ball and socket joints, or simply weak points formed in the rods 206-1 of the links 203b-1 (FIGS. 32 and 34), to facilitate movement in multiple directions. Alternatively, or in addition, all of the links in some contact array assemblies may be jointed.

Figure 85:
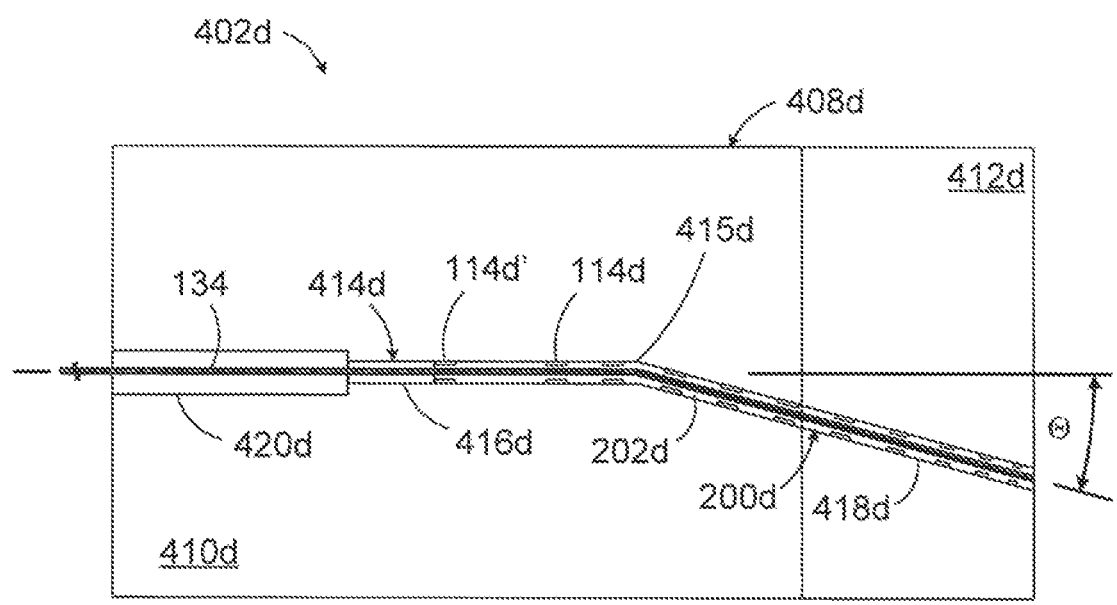
FIG. 85 is a plan view of the contact array assembly illustrated in FIG. 50 on a portion of the mold illustrated in FIG. 84.

It should also be noted here that the present cochlear leads with pre-set curvatures are not limited to curves that define a flat plane. By way of example, the present cochlear leads include cochlear leads with pre-set generally helical shape. One example of a mold that may be used to produce such is the mold 400d illustrated in FIGS. 84 and 85. The mold 400d is similar to mold 400c and similar elements are represented by similar reference numerals. To that end, the mold 400d includes mold parts 402d-406d, The mold part 402d includes a block 408d with straight and curved portions 410d and 412d. A semi-circular lead defining surface 414d, with straight and curved portions 416d and 418d, is formed in the straight and curved portions 410d and 412d of the block 408d. Unlike the mold 400c, however, the lead defining surface 414d includes at least one bend point 415d where the lead defining surface is redirected by an angle Θ. The lead defining surface portion 418d will, therefore, extend helically around the curved portion 412d of the block 408d. A semi-circular surface 420d with a shape corresponding to a portion of the wing 128 is also formed in the straight portion 410d. In some instances, a resilient insert (not shown) similar to the insert 412 described above with reference to FIGS. 22-27 may be provided. The mold parts 404d and 406d respectively include blocks 422c and 424c with semi-circular lead defining surfaces (not shown) which are coextensive with the lead defining surface 414d and, together with the lead defining surface 414d, define the mold cavity that is used to form a flexible body with a helical portion. The mold part 404d also includes a semi-circular surface (not shown) with a shape corresponding to a portion of the wing.

One example of a contact array assembly that may be inserted into the mold 400d and used to form a cochlear lead with pre-set generally helical shape is the contact array assembly 200d, as shown. Contact array assemblies with various combinations of the links 203b, the link 203e and/or the link 203f may also be employed.

As described in greater detail above, manufacture of the present contact array assemblies involves positioning the ends of a plurality of lead wires adjacent to the associated electrically conductive contacts or the workpieces that are used to form the contacts. The efficiency of this aspect of the manufacturing process may be improved through the use of wire holders that position the ends of the lead wires adjacent to the associated contacts or workpieces in such a manner that the ends of the lead wires may be readily pulled from the holder and positioned at the intended location.

Figure 86:
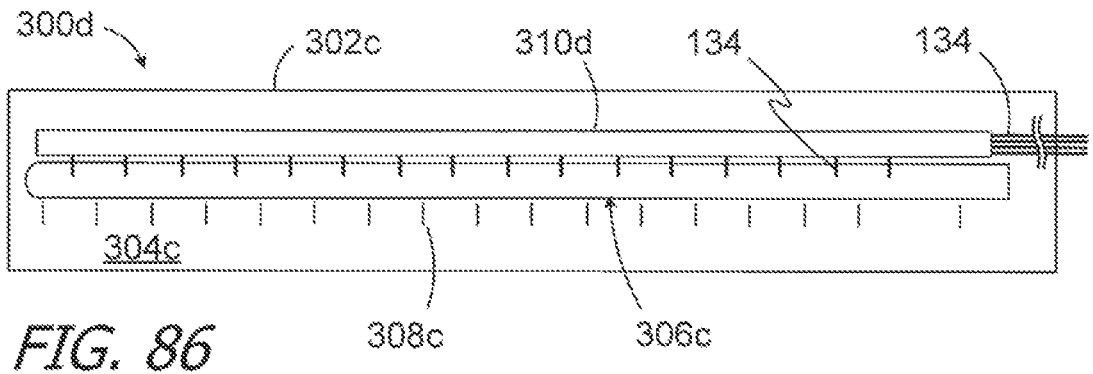
FIG. 86 is a plan view of a fixture in accordance with one embodiment of a present invention.
Figure 87:
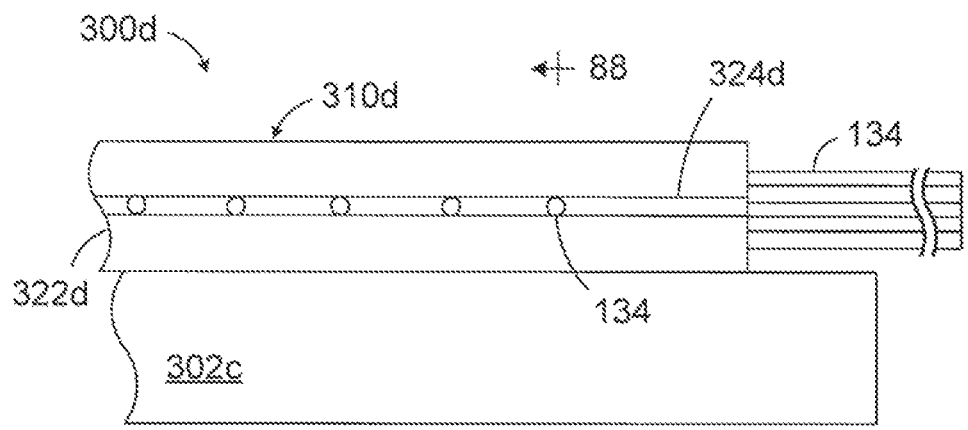
FIG. 87 is a side view the fixture illustrated in FIG. 86.
Figure 88:
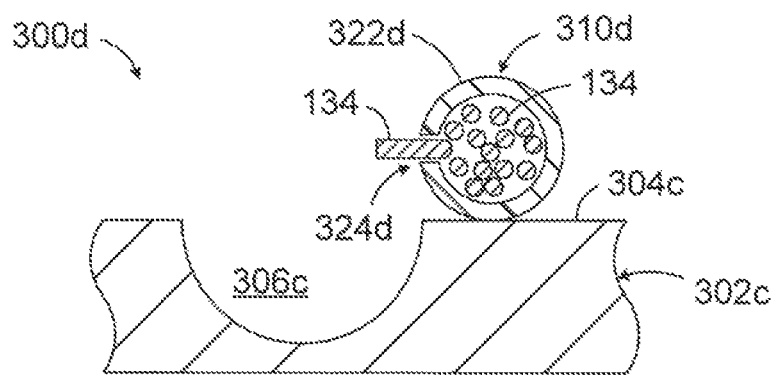
FIG. 88 is a section view taken along line 88-88 in FIG. 87.

One example of a fixture with such a wire holder is the exemplary fixture 300d illustrated in FIGS. 86-88. The fixture 300d is substantially similar to fixture 300c and similar elements are represented by similar reference numerals. For example, the fixture 300d includes the aforementioned plate 302c with a top surface 304c, an elongate cavity 306c, and a plurality of markers 308c. Here, however, the wire rest 310c has been omitted and replaced by a wire holder 310d. The exemplary wire holder 310d, which includes a tubular member 322d and a horizontal slot 324d that extends through the tubular member, may be secured to the top surface 304c of the plate 302c or simply held in place by the technician. Although not so limited, suitable materials for the tubular member 322d include silicone elastomers such as Silastic® silicone elastomer from Dow Corning.

The lead wires 134 may be positioned with the tubular member 322d in such a manner that the ends extend through the slot 324d at locations corresponding to the contacts. Such an arrangement allows portions of the lead wires 134 to be pulled through the slot 324d as needed (e.g., just prior to the compression of a workpiece). The remainders of the lead wires 134 may continue to be held by the holder 310d until all of the wires have been connected to contacts. In those instances where a carrier is to be formed (e.g., a carrier 202c), the holder 310d may be used to keep the wires out of the cavity 306c while resilient material is injected into the cavity in a manner similar to that described above in the context of the wire rest 310c and the contact array assembly 202c. The remainder of the lead wires 134 may then be pulled through the slot 324d and the holder 310d discarded or reused.

Figure 89:
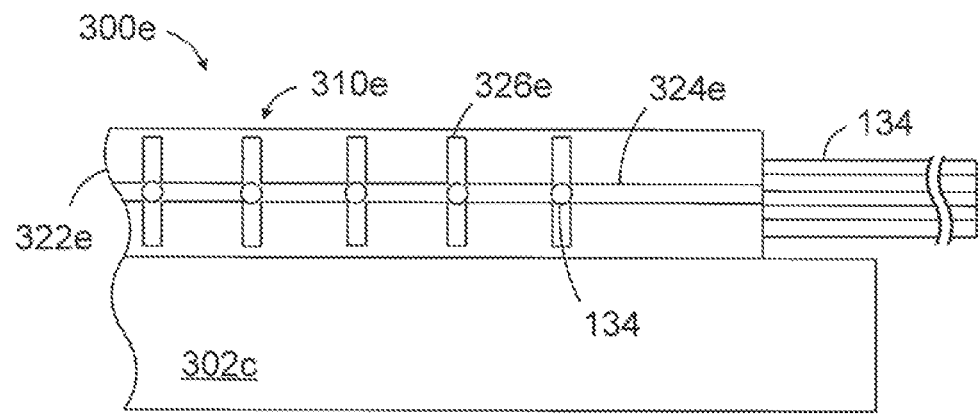
FIG. 89 is a side view of a fixture in accordance with one embodiment of a present invention.
Figure 90:
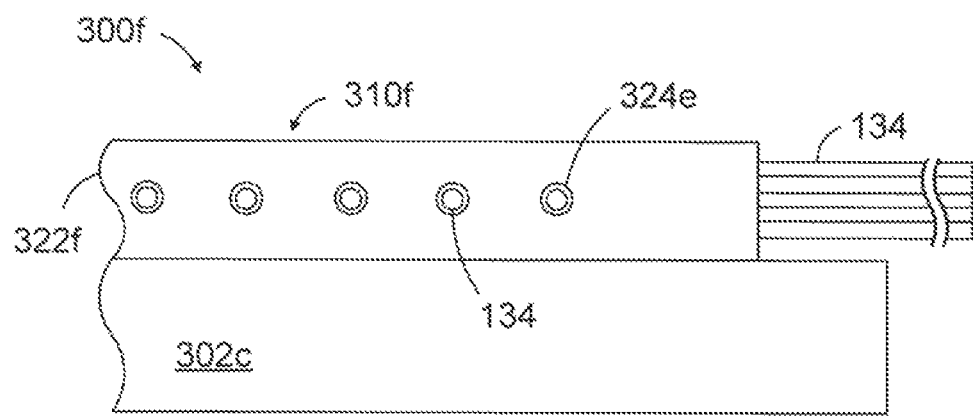
FIG. 90 is a side view of a fixture in accordance with one embodiment of a present invention.

Another exemplary fixture with a wire holder is the fixture 300e with a wire holder 310e illustrated in FIG. 89. The wire holder 310e includes a tubular member 322e with a horizontal slot 324e that extends through the tubular member. Vertical slots 324e, which facilitate accurate placement of the wire ends relative to the plate 302c, as well as relative to the contacts or workpieces on the plate, also extend through the tubular member 322e. Turning to FIG. 90, the exemplary fixture 300f includes a wire holder 310f with a tubular member 322f and a plurality of spaced apertures 324e through which the respective plurality of lead wire ends extend. The tubular member 322f, with the lead wires extending therethrough, may form part of the associated electrode array.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A method of forming a cochlear implant electrode array including a flexible body, a plurality of electrically conductive contacts on the flexible body and a plurality of lead wires respectively connected to the plurality of electrically conductive contacts, the method comprising the steps of:

forming a contact array assembly by
positioning the electrically conductive contacts and lead wires within a cavity of a fixture in such a manner that one end of each lead wire is connected to a respective electrically conductive contact and the remainder of each lead wire is located outside of the cavity of the fixture, and
forming a carrier that defines a portion of the flexible body by introducing resilient material into the cavity of the fixture while the remainder of each lead wire is located outside of the cavity of the fixture;
removing the contact array assembly from the cavity of the fixture;
positioning the contact array assembly in a curved mold with the remainders of the lead wires located outside of the carrier and free to move relative to the carrier; and
introducing resilient material into the curved mold to complete the flexible body.

2. A method as claimed in claim 1, wherein
the step of positioning the electrically conductive contacts and lead wires within a cavity of a fixture comprises
positioning a plurality of workpieces in the cavity of the fixture with one end of each lead wire located within a respective workpiece, and
compressing each workpiece to form the electrically conductive contacts and connect one end of a respective lead wire thereto.

3. A method as claimed in claim 1, wherein
the carrier defines a top surface; and
the step of positioning the contact array assembly in a curved mold comprises positioning the contact array assembly in a curved mold with the remainders of the lead wires located on the top surface of the carrier.

4. A method as claimed in claim 1, further comprising the step of:
directing the remainder of each lead wire over a wire rest that is located adjacent to the cavity of the fixture.

5. A method as claimed in claim 1, further comprising the step of:
positioning a tube on the contact array assembly prior to the step of introducing resilient material into the curved mold to complete the flexible body.

6. A method of forming a cochlear implant electrode array including a flexible body, a plurality of electrically conductive contacts on the flexible body and a plurality of lead wires respectively connected to the plurality of electrically conductive contacts, the method comprising the steps of:

forming a contact array assembly by
positioning the electrically conductive contacts within a cavity,
pulling one end of each lead wire out of a wire holder that is located adjacent to the cavity, while at least the portion of the remainder of each lead wire that is coextensive with the cavity remains within the wire holder and outside of the cavity, connecting the one end of each lead wire to a respective contact, and forming a carrier that defines a portion of the flexible body by introducing resilient material into the cavity while the remainder of each lead wire is located outside of the cavity;

positioning the contact array assembly in a curved mold with the remainders of the lead wires located outside of the carrier and free to move relative to the carrier; and introducing resilient material into the curved mold to complete the flexible body.

7. A method as claimed in claim 6, wherein the step of positioning the electrically conductive contacts comprises positioning a plurality of workpieces in the cavity with one end of each lead wire located within a respective workpiece, and the step of connecting the one end of each lead wire to a respective contact comprises compressing each workpiece to form the electrically conductive contacts and connect one end of a respective lead wire thereto.

8. A method as claimed in claim 6, wherein the carrier defines a top surface; and the step of positioning the contact array assembly in a curved mold comprises positioning the contact array assembly in a curved mold with the remainders of the lead wires located on the top surface of the carrier.

9. A method as claimed in claim 6, further comprising the step of:

directing the remainder of each lead wire over a wire rest that is located adjacent to the cavity.

10. A method as claimed in claim 6, further comprising the step of:

positioning a tube on the contact array assembly prior to the step of introducing resilient material into the curved mold to complete the flexible body.

\* \* \* \* \*